US009241960B2

(12) United States Patent
Reimann et al.

(10) Patent No.: US 9,241,960 B2
(45) Date of Patent: Jan. 26, 2016

(54) INFECTIOUS SCHMALLENBERG VIRUS FROM CLONED CDNAS AND USES THEREOF

(71) Applicants: Ilona Reimann, Gristow (DE); Martin Beer, Neuenkirchen (DE); Kerstin Wernike, Greifswald (DE)

(72) Inventors: Ilona Reimann, Gristow (DE); Martin Beer, Neuenkirchen (DE); Kerstin Wernike, Greifswald (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 92 days.

(21) Appl. No.: 13/904,506

(22) Filed: May 29, 2013

(65) Prior Publication Data

US 2013/0323210 A1 Dec. 5, 2013

(30) Foreign Application Priority Data

Jun. 1, 2012 (EP) .................................... 12170630

(51) Int. Cl.
*A61K 35/76* (2015.01)
*C12N 7/00* (2006.01)
*C12N 15/86* (2006.01)
*C07K 14/005* (2006.01)

(52) U.S. Cl.
CPC ............... *A61K 35/76* (2013.01); *C07K 14/005* (2013.01); *C12N 7/00* (2013.01); *C12N 15/86* (2013.01); *C12N 2760/12022* (2013.01); *C12N 2760/12043* (2013.01); *C12N 2760/12051* (2013.01)

(58) Field of Classification Search
None
See application file for complete search history.

(56) References Cited

U.S. PATENT DOCUMENTS

| | | | |
|---|---|---|---|
| 2008/0226682 | A1 | 9/2008 | Brake et al. |
| 2013/0323210 | A1 | 12/2013 | Reimann et al. |
| 2013/0323277 | A1 | 12/2013 | Nikolin et al. |

OTHER PUBLICATIONS

Bennett et al., A Recombinant Chimeric La Crosse Virus Expressing the Surface Glycoproteins of Jamestown Canyon Virus Is Immunogenic and Protective against Challenge with either Parental Virus in Mice or Monkeys, 2012, Journal of Virology, vol. 86, No. 1, pp. 420-426.*

Beer et al., "Update-Information from the Friedrich-Loeffler-Institut on 'Schmallenberg Virus': Accessions No of full-length sequences available". Friedrich-Loeffler-Institut, Jan. 16, 2012, 1 page. [Accessed at http://www.fli.bund.de/fileadmin/dam_uploads/tierseuchen/Schmallenberg_Virus/Schmallenberg-Update_20120116-en.pdf on Jul. 9, 2013].

Elliott et al., "Establishment of a reverse genetics system for Schmallenberg virus, a newly emerged orthobunyavirus in Europe". Journal of General Virology, vol. 94, No. 4, Apr. 2013, pp. 851-859.

EMBL Accession No. HE649913, Hoffman et al., "Schmallenberg virus gene for M polyprotein, segment M, genomic RNA, isolate BH80/11-4"., Frederick-Loeffler-Institute, Jan. 16, 2012, 3 pages.

EMBL Accession No. HE6499132, Hoffman et al., "Schmallenberg virus RdRp gene for RNA-dependent RNA polymerase, segment L, genomic RNA, isolate BH80111-4"., Frederick-Loeffler-Institute, Jan. 16, 2012, 4 pages.

EMBL Accession No. HE649914, Hoeper, D., "Schmallenberg virus genes for nucleocapsid protein and non-structural protein, segment S, genomic RNA, isolate BH80/11-4"., Frederick-Loeffler-Institute, Jan. 16, 2012, 2 pages.

Garigliany et al., "Schmallenberg virus: A new Shamonda/Sathuperi-like virus on the rise in Europe". Antiviral Research, vol. 95, No. 2, May 2012, pp. 82-87.

Hoffmann et al., "Novel Orthobunyavirus in Cattle, Europe, 2011". Emerging Infectious Diseases, vol. 18, No. 3, Mar. 2012, pp. 469-472.

Ikegami et al., "Rift Valley fever vaccines". Vaccine, vol. 27, Nov. 2009, pp. D69-D72.

Mettenleiter et al., "Information from the Friedrich-Loeffler-Institut on 'Schmallenberg Virus'". Friedrich-Loeffler-Institut, Jan 10, 2012, 1 page. [Accessed at http://www.fli.bund.de/fileadmin/dam_uploads/tierseuchen/Schmallenberg_Virus/FLIInformation_Schmallenberg-20120110.pdf on Jul. 9, 2013].

Varela et al., "Schmallenberg Virus Pathogenesis, Tropism and Interaction with the Innate Immune System of the Host". PLOS Pathogens, vol. 9, No. 1, e1003133, Jan. 2013, pp. 1-13.

Wernike et al., "Inactivated Schmallenberg virus prototype vaccines". Vaccine, vol. 31, May 2013, pp. 3558-3563.

Wernike et al., "Schmallenberg virus challenge modesl in cattle: infectious serum or culture-grown virus". Veterinary Research, vol. 43, No. 1, Dec. 2012, pp. 84-87.

Yanase et al., "Genetic reassortment between Sathuperi and Shamonda viruses of the genus Orthobunyavirus in nature: implications for their genetic relationship to Schmallenberg virus". Archives of Virology, vol. 157, No. 8, May 2012, pp. 1611-1616.

Bridgen et al., "Rescue of a segmented negative-strand RNA virus entirely from cloned complementary DNAs". Procedures of the National Academy of Sciences, vol. 93, Dec. 1996, pp. 15400-15404.

Lytle et al., "Predicted Inactivation of Viruses of Relevance to Biodefense by Solar Radiation". Journal of Virology, vol. 79, No. 22, Nov. 2005, pp. 14244-14252.

* cited by examiner

*Primary Examiner* — Benjamin P Blumel

(74) *Attorney, Agent, or Firm* — Michael P. Morris; Wendy M. Gombert

(57) ABSTRACT

The present invention belongs to the field of animal health and relates to a nucleic acid sequence which comprises the complete genome of an infectious Schmallenberg virus (SBV) useful for studying viremia and diseases caused by SBV in ruminants, and in the development of vaccines, therapeutics and diagnostics for the prophylaxis, treatment and diagnosis of viremia and diseases caused by SBV.

16 Claims, 6 Drawing Sheets

Figure 1A:
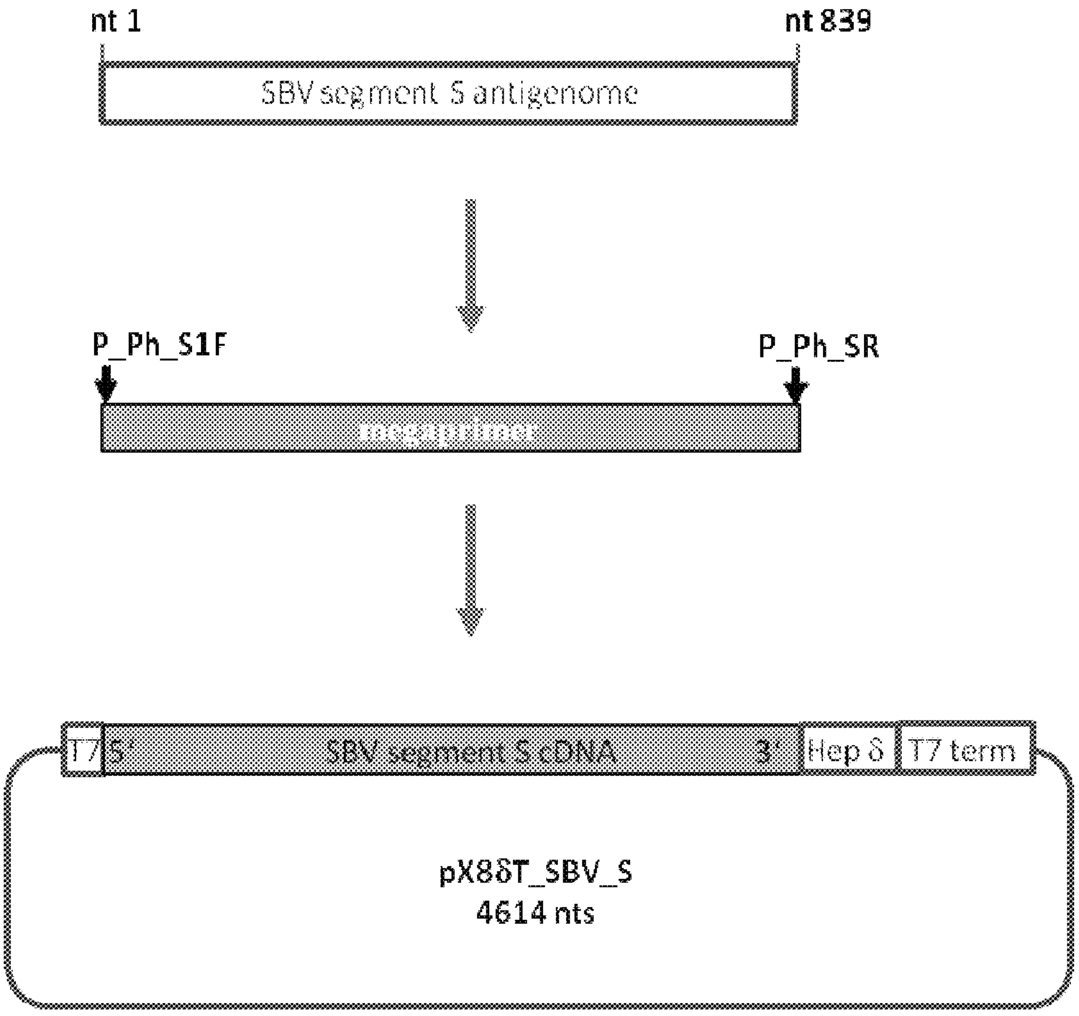

Construction of the plasmid pX8dT_SBV_S.

Construction of the plasmid pX8dT_SBV_M.

Construction of the plasmid pX8dT_SBV_L.

Construction of the plasmid pT7ribo_SBV_S

Schmallenberg-Virus cRNA Segment S (nt 1 – nt 839)

P_Ph_S1F → PCR fragment ← P_Ph_SR pX8δT_SBV_S
4614 nts
(T7 5' – SBV Segment S cDNA – 3' – Hep δ – T7 term)

P_Ph_S2F → PCR fragment ← P_Ph_SR pT7ribo_SBV_S
3991 nts
(T7 5' – SBV Segment S cDNA – 3' – Hep δ – T7 term)

Construction of the plasmid pT7ribo_SBV_M

Construction of the plasmid pT7ribo_SBV_L

SEQUENCE LISTING

```
<160> NUMBER OF SEQ ID NOS: 10

<210> SEQ ID NO 1
<211> LENGTH: 839
<212> TYPE: DNA
<213> ORGANISM: Schmallenberg virus

<400> SEQUENCE: 1

agtagtgagc tccactatta actacagaaa tatgtcaagc caattcattt ttgaagatgt      60

accacaacgg aatgcagcta catttaaccc ggaggtcggg tatgtggcat ttattggtaa     120

gtatgggcaa caactcaact tcggtgttgc tagagtcttc ttcctcaacc agaagaaggc     180

caagatggtc ctacataaga cggcacaacc aagtgtcgat cttacttttg gtggggtcaa     240

atttacagtg gttaataacc attttcccca atatgtctca aatcctgtgc cagacaatgc     300

cattacactt cacaggatgt caggatatct agcacgttgg attgctgata catgcaaggc     360

tagtgtcctc aaactagctg aagctagtgc tcagattgtc atgccccttg ctgaggttaa     420

gggatgcacc tgggccgatg gttatacaat gtatcttgga tttgcacctg gggccgaaat     480

gttccttgat gcttttgact tctatccact agttattgaa atgcataggg tcctcaagga     540

caatatggat gtaaatttta tgaaaaaagt cctccgccaa cgctatggaa caatgactgc     600

tgaagaatgg atgactcaga aaataacaga aataaaagct gcttttaatt ctgttggaca     660

gcttgcctgg gccaaatctg gattctctcc tgctgctaga accttcttgc agcaattcgg     720

tatcaacatc taaacctctt catcacagat cttcaatttc cgtgcaatat gtctatgtat     780

tgcacaccat tatactgcaa ggcttctgtt aagatagtta ataagtggag aacactact      839
```

-continued

<210> SEQ ID NO 2
<211> LENGTH: 4373
<212> TYPE: DNA
<213> ORGANISM: Schmallenberg virus

<400> SEQUENCE: 2
agtagtgaac taccacaatc aaaatgcttc tcaacattgt cttgatatct aacttagcct 60
gtttagcttt tgcactccca cttaaggaag gcactagagg gtctaggtgc ttcctgaatg 120
gcgaactggt taaaactgtt aacacatcaa aggtcgtttc agaatgctgt gtgaaagacg 180
acatatctat cattaaatca aatgctgaac attataaatc aggagatcgg ttggctgctg 240
taataaaata ttatcgttta tatcaggtga aggattggca ttcttgcaat ccaatttatg 300
atgaccacgg ttcctttatg atattagata tagataatac tggcacatta atccctaaaa 360
tgcatacatg cagagttgaa tgcgaaatag cactgaataa agatactggc gaagttatat 420
tgaattcata tcgaattaac cactaccgaa tctcgggcac aatgcatgta tcaggttggt 480
ttaaaaacaa aattgagatt cctttggaaa acacatgcga atccattgag gtaacatgtg 540
gattaaaaac acttaatttt catgcatgtt tccataccca taagtcatgc acccgctatt 600
ttaaaggatc aatcctgccg gaattgatga tcgaatcatt ttgtacgaat cttgaattaa 660
tactgctagt aactttcata ttagttgggt ctgtcatgat gatgatattg acgaaaacat 720
atatagtata tgtgttcatt cctatatttt atccatttgt gaaattatat gcttatatgt 780
acaacaaata ttttaaattg tgtaaaaatt gcctgttagc agtacatccc tttacaaatt 840
gcccatcgac atgcatctgt ggaatgattt acactaccac tgaatcactc aaattgcatc 900
gcatgtgtaa caattgttct ggctataaag cattgccgaa aacaaggaaa ttgtgtaaaa 960
gtaaaatatc caatatagtg ctatgtgtga taacatcact gatatttttc tcatttatca 1020
cacctatatc gagtcaatgt atcgatatag aaaaactgcc agacgagtat attacatgta 1080
aaagagagct agctaatatc aaaagcttga caattgatga cacatatagc tttatatatt 1140
cctgtacatg cataattgtg ttaatattac ttaaaaaggc agcaaagtat atcttgtact 1200
gcaactgcag cttttgtggt atggtacatg aacgacgtgg attgaagata atggacaact 1260
ttacaaacaa gtgcctaagt tgtgtatgcg cagaaaacaa gggcttaaca attcacagag 1320
cctctgagaa atgtctgttc aaatttgaat caagttataa taggaccggg ttgataatct 1380
ttatgcttct gttagtccca acaattgtaa tgacgcaaga aactagtatt aactgcaaaa 1440
acattcaatc aactcagctt acaatagagc acctgagtaa gtgcatggca ttttatcaaa 1500
ataaaacaag ctcaccagtt gtaatcaatg aaataatttc agatgcttca gtagacgaac 1560
aagaattaat aaaaagttta aacttgaact gtaatgtcat agataggttt atttccgaat 1620
ctagtgttat tgagactcaa gtttattatg agtatataaa atcacagttg tgccctctcc 1680
aagtgcatga tattttcact atcaattcag caagtaacat acaatggaaa gcactggccc 1740
gaagtttcac cttaggagtg tgcaatacga atcctcataa acatatatgt agatgcttgg 1800
agtctatgca aatgtgcaca tcaaccaaga cagaccacgc tagggaaatg tcaatatatt 1860
atgatggtca tccagatcgc tttgagcatg acatgaaaat aatattgaat ataatgagat 1920
atatagtccc tggattaggt cgagtcttgc ttgatcaaat caaacaaaca aaagactacc 1980
aagctttacg ccacatacaa ggtaagcttt ctcctaaatc gcagtcaaat ttacaactta 2040
aaggatttct ggaatttgtt gattttatcc ttggtgcaaa cgtgacaata gaaaaaaccc 2100
ctcaaacatt aactacatta tctttgataa aaggagccca cagaaacttg gatcaaaaag 2160

-continued

```
atccaggtcc aacaccaata ctggtatgca aatcaccaca aaaagtggta tgctactcac   2220

cacgtggtgt cacacaccca ggagattata tatcatgcaa atctaagatg tataagtggc   2280

catctttagg ggtatacaaa cataatagag accagcaaca agcctgcagc agtgacacac   2340

attgcctaga gatgtttgaa ccagcagaaa gaacaataac tacaaaaata tgcaaagtaa   2400

gtgatatgac ttattcagaa tcgccatata gtactggaat accatcatgc aacgtgaaga   2460

gatttggatc atgtaatgta aggggtcatc aatggcaaat tgcagaatgc tcaaatggct   2520

tattttacta tgtttcagct aaagcccatt cgaaaactaa cgatataaca ctgtactgtt   2580

tatcagcaaa ttgcctggac ttgcgttatg cattcagatc cagtagttgt tcagatatag   2640

tatgggatac aagttatcga aataaattaa cacctaaatc tattaatcat ccagatattg   2700

aaaactacat agcagcgctt cagtcagata ttgcaaatga tttaactatg cactacttta   2760

aaccattaaa aaaccttcca gcaataattc ctcaatacaa aacaatgaca ttgaatgggg   2820

acaaggtatc aaatggtatt agaaatagtt atatcgagtc gcacatccct gcaattaatg   2880

gtttatcagc agggattaat attgccatgc caaatggaga aagcctcttt tccattatta   2940

tctatgtcag aagagtaata aataaagcat cgtatcgatt tctatatgaa acaggaccca   3000

caattggaat aaatgccaag cacgaagagg tatgtaccgg gaagtgccca agcccaatac   3060

cacatcaaga tggttgggtc acattctcaa aggaaagatc aagtaattgg ggctgtgaag   3120

aatggggttg cttggcaata aatgatggtt gtttatatgg gtcatgtcaa gacataataa   3180

ggcctgaata taagatatac aagaagtcta gtattgaaca aaaggatgtt gaagtttgta   3240

taaccatggc ccatgaatca ttctgcagta ccgttgatgt tctccaacct ttaattagcg   3300

acaggataca attagatatc caaacgattc aaatggactc tatgccaaat ataattgcag   3360

tcaagaatgg gaaagtttat gttggagata tcaatgactt aggttcgaca gcaaagaaat   3420

gtggctcagt ccaattatat tctgaaggga tcattggatc gggaacccca aaatttgatt   3480

atgtttgcca tgcattcaat cgtaaagatg tcatccttcg aagatgcttt gataactcat   3540

atcagtcttg tcttctcttg gaacaagata atacattaac tattgcttct accagtcata   3600

tggaagtgca taaaaaagtt tcaagcgtgg gtacaatcaa ttataaaatt atgttagggg   3660

attttgacta caatgcatat tcaacacaag caacagtcac aatagatgag atcaggtgtg   3720

gtggttgtta tggctgccct gaaggaatgg cttgcgcact caaattgagt accaatacca   3780

tcgggagttg ttcaataaaa agtaactgcg atacatacat taaaataata gcagtcgatc   3840

cgatgcagag cgagtattcc attaagttaa actgcccact agcaacagag acagtttcag   3900

taagtgtgtg ctcagcttct gcttacacaa aaccttcaat atctaaaaat caaccaaaaa   3960

ttgttttgaa ttccttagat gaaacatctt acatcgagca acatgataaa aagtgttcta   4020

catggctttg cagagtttat aaagaaggga ttagcgtaat atttcagcct ctatttggca   4080

acctatcttt ctattggaga ctgacaatat atataataat ctctttgatt atgctaattc   4140

tgtttctata catattaata ccactgtgca aacggctaaa aggtttattg gaatacaatg   4200

agagaatata ccaaatggaa aataaattta agtgataagc cttataacaa tgagcaatta   4260

taaatgaata aataaaaaca ataaaagata aacaaataac aacatatata tgtggttaca   4320

catatatatg taattattca gctgagaagt ttttcatgtg gtagaacact act          4373
```

<210> SEQ ID NO 3
<211> LENGTH: 6882
<212> TYPE: DNA
<213> ORGANISM: Schmallenberg virus

<400> SEQUENCE: 3

```
agtagtgtac ccctaattac aatcactatg gagacataca agattaacat ttttagagat      60
aggatcaacc agtgtcgaag tgctgaagaa gccaaagaca ttgttgctga tcttctcatg     120
gctagacatg actactttgg tagagaggta tgttattacc tggatatcga attccggcag     180
gatgttccag cttacgacat acttcttgaa tttctgccag ctggcactgc tttcaacatt     240
cgcaattgta caccagacaa ttttatcatt cacaatggca agctttatat cattgactat     300
aaagtatcaa ctgatcatgc atatggtcaa aaaacttatg aaaagtacac ccagatcttt     360
ggagacgcat tgtcagaatt gccgtttgat tttgaagttg tgatcatccg tgctgaccct     420
ctgcgagata ctatccatgt taattcaaat caattcttgg aaatatttgg gccgctcaac     480
ataaaccttg attttacttg gttctttaat ttgcgatccc tgatatatga gaaatataag     540
gatgacgaca gattcctaga aattgtgaat caaggtgaat ttacgatgac tggaccctgg     600
attgatgagg ataccccgga gctctattca caccctgtct tttggaatt ctatgattct      660
ttagatgaga tggctaaact gacattccat gagtctatga catttgatgc aactcgcggt     720
gagaaatgga atcaaaatct acaaaaggtt ataaatagat atggcaatga ttataacatt     780
tttgtgaaag aggccgctgc aggaatcttt agatgtgaag ggaactaccc aaaaccaaat     840
catgatgaaa tcacaatcgg ttggaatcaa atggttcaaa gagtgagtac tgagagaaac     900
ctgactcaag atgtcagcaa gcaaaaacca tctattcatt tcatatgggg tcaacctgac     960
gaaacatcaa atgcgacaac accaaaacta atcaagattg caaaagcact ccaaaatatt    1020
tctggcgagt ctacatatat aagcgcattc agagcattgg gtatgcttat ggacttttct    1080
gagaacacag ctttatatga agcacacact agcaaactaa aaagtatggc aagacagaca    1140
tcgaaaagaa ttgatactaa actggaacca atcaaaatag gcacggcgac aatttattgg    1200
gaacagcagt ttaaactgga tactgaaata atgaatacaa aagacaaatc acatttgcta    1260
aaagattttc ttggcatagg gggtcacgtg caattttcaa aaaagaccat tgacgatttg    1320
gatactgaca aacctactat attagatttc aacaaaaagg aagtcattga tttttgcaaa    1380
ttccagtatg aaaatgtaaa gaaaatacta tccggagata ataatctaga gcgtatagga    1440
tgttatttag aagaatatgg tgcaaatatt gcatcatgtt caaaggatac atgggatcag    1500
attaaccaga tagggaagtc aaattactgg gcttgtatta aagatttttc agtcttgatg    1560
aaaaatatgt tggcagtttc tcaatataat aggcacaata cttttcgtgt agtgtgttgt    1620
gcaaacaata atctgtttgg gtttgtaatg ccttcttctg atattaaagc aaagcgatcc    1680
acacttgttt acttcttagc tgtgttgcat tctactcctc agaatgtgat gcaccacggt    1740
gcattgcatg cgacatttaa aactggttca aaatacctta gtatctctaa aggaatgcgt    1800
ttagataaag aacgatgtca acgcatagtt agttcaccgg gactttttat gttgactaca    1860
ttgatgtttg caggagacaa tccgacactc aatttgactg atgtcatgaa ttttacattc    1920
cacacttccc tgtctataac caaagctatg ctgtcattga cagaaccatc aagatatatg    1980
ataatgaatt cattagccat atccagtcat gttagagatt atatagcaga aaaatttggc    2040
ccttatacaa agaccagctt ctctgtagta atggcaaact tgattaaaag gggatgttat    2100
atggcatata atcaaagaga taaagtagac atgaggaata tctgcctaac agattatgaa    2160
ataactcaaa aaggtgtgag agataacaga gacctatcat caatctggtt tgaaggctat    2220
gtatcactaa aagaatatat taaccaaata tatctaccat tttacttcaa ttcaaaaggt    2280
ttgcatgaaa agcatcatgt tatgatagat ctggctaaga caatcttaga tatagaaagg    2340
```

-continued

```
gaccagagat taaatatccc aggaatatgg tctacaacac ctagaaaaca aactgcaaat   2400
ttaaatataa ctatctatgc agttgcaaaa aatctaataa tggacactgc tagacataat   2460
tatattagat cacggataga aaacacaaac aacttaaata gatcgatatg cactatttct   2520
acattcacca gctctaaatc atgtattaaa gtaggcgact ttgagaaaga aaaaagctca   2580
gcaacaaaaa aggctgcaga ttgcatgtca aaagagataa agaagtatac aattgcaaac   2640
ccagaatttg ttgatgaaga gttactaaat gcaactataa gacattcacg ctatgaagac   2700
ttaaaaaaag caatcccgaa ttatattgac attatgtcaa ctaaagtatt tgattctctg   2760
taccagaaaa taaaaaggaa ggagatagat gataaaccca ctgtgtatca tatactctct   2820
gctatgaaga atcacacaga ttttaagttt acattcttta acaaaggcca aaaaacagca   2880
aaggataggg aaatattcgt aggcgaattt gaggcaaaaa tgtgcttgta tttagtggag   2940
aggatatcta aagaacgctg taagttgaat ccagatgaga tgattagtga accaggcgat   3000
tctaaattga aaaaattaga agagcttgca gagtctgaaa tacgattcac agcagcaact   3060
atgaaacaga tcaaagaacg ctatttagca gaaatgggag aagcaagcca tatgatcgca   3120
tataaaccac attctgttaa gattgaaatc aatgcagaca tgtcaaaatg gagtgcccaa   3180
gatgttttat tcaaatattt ctggttgttt gcattagatc ccgcacttta tctgcaagaa   3240
aaagaaagga tattgtactt cctatgcaat tatatgcaaa aaaagctaat tctgcctgat   3300
gaaatgctct gtagcatcct tgaccaacgt atcaaacatg aggatgatat aatatatgaa   3360
atgaccaatg gcttatcgca aaattgggtc aatattaaac ggaactggct gcaggggaat   3420
ctcaattaca caagtagcta cctacattca tgttctatga atgtttataa ggatattcta   3480
aagagagcag ccactttact agaaggggaa gttttagtca attctatggt tcattctgat   3540
gacaatcaca cttcaatagt gatgatccaa gataaattag atgatgatat tgttattgaa   3600
ttttctgcaa aactatttga aaaaatatgt ctaacttttg gaaatcaagc aaatatgaag   3660
aagacatata taacaaattt cataaaggag ttcgtttcac tttttaatat ttatggtgag   3720
ccattttctg tttatggtcg ctttattttg acatctgttg gcgattgtgc ttttcttgga   3780
ccatatgagg atgttgccag taggttgtct gcaacgcaga cagcaattaa gcatggagca   3840
cctccatcac ttgcatggac tgctattgca ttaactcagt ggataacaca tagcacatat   3900
aacatgcttc caggtcaaat caatgatcct acttcatctt tacctagtca tgatagattt   3960
gagctgccta tagaattgtg tggcttaata aattcagaat tacccactat agctatagca   4020
ggtttggaag cagataatct aagttattta gttaggttat caaaaagaat gtcccctata   4080
catctttgcc gtgaaccaat ccagcatcaa tatgagaata tacatacatg ggatataagt   4140
aaactgacac aatgtgatat tttcagactt aagcttttaa gatacatgac gttagactca   4200
actatgtcat ctgatgatgg aatgggcgaa actagtgaaa tgagatctag gtctcttctg   4260
acaccaagaa aattcactac tgcaagttcg ttatctagat tgcattcata tgctgattat   4320
caaaaaacaa tacaagacca acagaaaatt gaagaattat ttgaatattt tatagccaac   4380
cctcaactat tggttacaaa aggtgagact tgtgaagagt tctgtatgtc tgtattgttc   4440
agatacaaca gtcgtaaatt taaagaatca ttgtctattc aaaacccagc tcagctcttc   4500
atagaacaag tattgtttgc aaataaacca atgatagact atacaagtat tcatgatagg   4560
ttgtttggta tacaagatga cccaaatata aatgatgcta catgtattat tggcaagaag   4620
acttttgttg aaacatatca gcaaataaaa attgatgtag aaaaatttac acttgatgta   4680
gaggatataa agacgatata tagcttctgt ataatgaacg accctatatt agttgcttgt   4740
```

-continued

```
gcaaacaact tgttaatttc aatacaggga gtggagatgc aacgattggg tatgacatgc   4800
tgttatatgc cggagattaa gagccttaaa gtaatttatc atagtcctgc tctcgtatta   4860
cgtgcttatg taacagataa ctatgagcaa aaagggatgg agccagatga aatgcggaga   4920
gatatatatc atttagaaga atttatagag aagacaaaat tgaggacaaa tatgcaaggg   4980
agaattgcaa ataatgaaat taagttaatg aagcgagatt tgaaatttga agtgcaggaa   5040
ttgactaaat tctatcagat ctgttatgaa tatgtgaaat caacagaaca caaaattaaa   5100
atattcatcc ttccaaaaaa ggcttacact cccattgatt tctgctcatt agtaacaggt   5160
aatctgatat cagacaacaa atggatggtt gttcactatt taaaacaaat aactgtccca   5220
gcaaagaagg cacaaatagc cacatctata gatctggaaa tacaaatagc ctacgaatgt   5280
ttcaggctaa ttgcacattt tgctgatatg ttcctaaatg atgactccaa aaaagcttat   5340
attaatgcaa ttattaacac atatacatac aaggatgttc aagtatccag tctctacaag   5400
aaaatcaaaa attcgagact acgttcaaaa attataccat tattatatca cctgggcgat   5460
ttgcaacaaa tagacgttga cagatttgat gcagaaaaag cagaagagca gatcacatgg   5520
aataactggc aaacatctcg agaatttact actggtccaa ttgatctatc aatcaaaggt   5580
tatggacggt caataaggat cgtaggtgag gacaacaagc ttacagctgc agaaatgcaa   5640
ttgtcaagag tgagaagtga tatagtatca aggcatggac aggctttatt gaacaaacct   5700
catgggctaa aattagagaa aatggaacca gtgactgatc taaatcctaa attatggtat   5760
attgcatacc aattgcgtga gaaaaagcgg tatcactatg ggtctttag tacatcttat    5820
atagaagagc ataactcaag gatagaagca tctcggatac gtaagactaa taaatggata   5880
ccagtttgcc ctattgctat atcaaaacaa tcatctgatg gaaagcctag tcttgcaaaa   5940
atccctatgt taaatattgg ggagattaaa tttacaaaac tacagattgc agtagatgat   6000
catgcaatga ttaggaaagc cccatttagt aagatggtgt tctttgatgg cccacccata   6060
cagagcggtg gcattgacat tggaaagctt atgaagaacc aaaatattct caatttgagg   6120
ttagataata tacagagtat aacattatta gatttgtgcc gcatattttc atgccgaggg   6180
tctaaagtgg atcaagatgc atttgaattc ttatctgatg aacctttgga tgaagatgtt   6240
attgatgaat tagatagctc acctgcatta gtggtatctt acacaaagaa atcaaccaaa   6300
tccaatagtt tcaaaaatgt tatagttaga gcattgataa gagaatgtga tatatttgaa   6360
gatataatgg acataacaga cgatggattc acatctgata gcaatctaga ggtgttagaa   6420
aacttaacat ggattttaaa tatgctcgca acaaatcagt ggtctacaga actgttagca   6480
tgcatacaca tgtgtttata tcgcaatgag atggatcata tctatcacaa ttttcaagtt   6540
ccagaaatat ttgtcgacaa tccaatctca ttaaatgtaa agtgggatga agtaattatg   6600
ttcttaaaca tactgcgaga cagagattac aaatttgagc catgggtgtc tatactgaat   6660
cattccttaa ctaaagctat agagtatgct tacaaaaaga tggaagagga gaggaagcag   6720
aaatcaacag gcatcaacaa attcttaaag ggtaaaaaaa tgggtggcag atcaaagttt   6780
gatttccagt agcttgatct taaataatac ataatctttg ccccaaatct gtattatata   6840
aataattcta aagtagtttc atgtaattag gggcacacta ct                      6882
```

<210> SEQ ID NO 4
<211> LENGTH: 4614
<212> TYPE: DNA
<213> ORGANISM: Artificial
<220> FEATURE:
<223> OTHER INFORMATION: Plasmid -continued

<400> SEQUENCE: 4

```
gacgcgccct gtagcggcgc attaagcgcg gcgggtgtgg tggttacgcg cagcgtgacc     60
gctacacttg ccagcgccct agcgcccgct cctttcgctt tcttcccttc ctttctcgcc    120
acgttcgccg gctttccccg tcaagctcta aatcgggggc tccctttagg gttccgattt    180
agtgctttac ggcacctcga ccccaaaaaa cttgattagg gtgatggttc acgtagtggg    240
ccatcgccct gatagacggt ttttcgccct ttgacgttgg agtccacgtt ctttaatagt    300
ggactcttgt tccaaactgg aacaacactc aaccctatct cggtctattc ttttgattta    360
taagggattt tgccgatttc ggcctattgg ttaaaaaaat gagctgattt aacaaaaatt    420
taacgcgaat tttaacaaaa tattaacgct tacaatttcc attcgccatt caggctgcgc    480
aactgttggg aagggcgatc ggtgcgggcc tcttcgctat tacgccagct ggcgaaaggg    540
ggatgtgctg caaggcgatt aagttgggta acgccagggt tttcccagtc acgacgttgt    600
aaaacgacgg ccagtgagcg cgcgataagc ttgtaatacg actcactata gggagtagtg    660
agctccacta ttaactacag aaatatgtca agccaattca tttttgaaga tgtaccacaa    720
cggaatgcag ctacatttaa cccggaggtc gggtatgtgg catttattgg taagtatggg    780
caacaactca acttcggtgt tgctagagtc ttcttcctca accagaagaa ggccaagatg    840
gtcctacata agacggcaca accaagtgtc gatcttactt ttggtggggt caaatttaca    900
gtggttaata accattttcc ccaatatgtc tcaaatcctg tgccagacaa tgccattaca    960
cttcacagga tgtcaggata tctagcacgt tggattgctg atacatgcaa ggctagtgtc   1020
ctcaaactag ctgaagctag tgctcagatt gtcatgcccc ttgctgaggt taagggatgc   1080
acctgggccg atggttatac aatgtatctt ggatttgcac ctggggccga aatgttcctt   1140
gatgcttttg acttctatcc actagttatt gaaatgcata gggtcctcaa ggacaatatg   1200
gatgtaaatt ttatgaaaaa agtcctccgc caacgctatg gaacaatgac tgctgaagaa   1260
tggatgactc agaaaataac agaaataaaa gctgctttta attctgttgg acagcttgcc   1320
tgggccaaat ctggattctc tcctgctgct agaaccttct tgcagcaatt cggtatcaac   1380
atctaaacct cttcatcaca gatcttcaat ttccgtgcaa tatgtctatg tattgcacac   1440
cattatactg caaggcttct gttaagatag ttaataagtg gagaacacta ctgggtcggc   1500
atggcatctc cacctcctcg cggtccgacc tgggcatccg aaggaggacg cacgtccact   1560
cggatggcta agggaggggc ggggatccgg ctgctaacaa agcccgaaag gaagctgagt   1620
tggctgctgc caccgctgag caataactag cataacccct tggggcctct aaacgggtct   1680
tgaggggttt tttgctgaaa ggaggaacta tatccggatc cactagttct agagcggccg   1740
ccaccgcggt ggagctccag cttttgttcc ctttagtgag ggttaattgc gcgcttggcg   1800
taatcatggt catagctgtt tcctgtgtga aattgttatc cgctcacaat tccacacaac   1860
atacgagccg gaagcataaa gtgtaaagcc tggggtgcct aatgagtgag ctaactcaca   1920
ttaattgcgt tgcgctcact gcccgctttc cagtcgggaa acctgtcgtg ccagctgcat   1980
taatgaatcg gccaacgcgc ggggagaggc ggtttgcgta ttgggcgctc ttccgcttcc   2040
tcgctcactg actcgctgcg ctcggtcgtt cggctgcggc gagcggtatc agctcactca   2100
aaggcggtaa tacggttatc cacagaatca ggggataacg caggaaagaa catgtgagca   2160
aaaggccagc aaaaggccag gaaccgtaaa aaggccgcgt tgctggcgtt tttccatagg   2220
ctccgccccc ctgacgagca tcacaaaaat cgacgctcaa gtcagaggtg gcgaaacccg   2280
acaggactat aaagatacca ggcgtttccc cctggaagct ccctcgtgcg ctctcctgtt   2340
```

-continued

```
ccgaccctgc cgcttaccgg atacctgtcc gcctttctcc cttcgggaag cgtggcgctt   2400

tctcatagct cacgctgtag gtatctcagt tcggtgtagg tcgttcgctc caagctgggc   2460

tgtgtgcacg aaccccccgt tcagcccgac cgctgcgcct tatccggtaa ctatcgtctt   2520

gagtccaacc cggtaagaca cgacttatcg ccactggcag cagccactgg taacaggatt   2580

agcagagcga ggtatgtagg cggtgctaca gagttcttga agtggtggcc taactacggc   2640

tacactagaa ggacagtatt tggtatctgc gctctgctga agccagttac cttcggaaaa   2700

agagttggta gctcttgatc cggcaaacaa accaccgctg gtagcggtgg tttttttgtt   2760

tgcaagcagc agattacgcg cagaaaaaaa ggatctcaag aagatccttt gatcttttct   2820

acggggtctg acgctcagtg gaacgaaaac tcacgttaag ggattttggt catgagatta   2880

tcaaaaagga tcttcaccta gatcctttta aattaaaaat gaagttttaa atcaatctaa   2940

agtatatatg agtaaacttg gtctgacagt taccaatgct taatcagtga ggcacctatc   3000

tcagcgatct gtctatttcg ttcatccata gttgcctgac tccccgtcgt gtagataact   3060

acgatacggg agggcttacc atctggcccc agtgctgcaa tgataccgcg agacccacgc   3120

tcaccggctc cagatttatc agcaataaac cagccagccg gaagggccga gcgcagaagt   3180

ggtcctgcaa ctttatccgc ctccatccag tctattaatt gttgccggga agctagagta   3240

agtagttcgc cagttaatag tttgcgcaac gttgttgcca ttgctacagg catcgtggtg   3300

tcacgctcgt cgtttggtat ggcttcattc agctccggtt cccaacgatc aaggcgagtt   3360

acatgatccc ccatgttgtg caaaaaagcg gttagctcct tcggtcctcc gatcgttgtc   3420

agaagtaagt tggccgcagt gttatcactc atggttatgg cagcactgca taattctctt   3480

actgtcatgc catccgtaag atgcttttct gtgactggtg agtactcaac caagtcattc   3540

tgagaatagt gtatgcggcg accgagttgc tcttgcccgg cgtcaatacg ggataatacc   3600

gcgccacata gcagaacttt aaaagtgctc atcattggaa aacgttcttc ggggcgaaaa   3660

ctctcaagga tcttaccgct gttgagatcc agttcgatgt aacccactcg tgcacccaac   3720

tgatcttcag catcttttac tttcaccagc gtttctgggt gagcaaaaac aggaaggcaa   3780

aatgccgcaa aaaagggaat aagggcgaca cggaaatgtt gaatactcat actcttcctt   3840

tttcaatatt attgaagcat ttatcagggt tattgtctca tgagcggata catatttgaa   3900

tgtatttaga aaaataaaca aataggggtt ccgcgcacat ttccccgaaa agtgccacct   3960

ggacgcgccc tgtagcggcg cattaagcgc ggcgggtgtg gtggttacgc gcagcgtgac   4020

cgctacactt gccagcgccc tagcgcccgc tcctttcgct ttcttccctt cctttctcgc   4080

cacgttcgcc ggctttcccc gtcaagctct aaatcggggg ctccctttag ggttccgatt   4140

tagtgcttta cggcacctcg accccaaaaa acttgattag ggtgatggtt cacgtagtgg   4200

gccatcgccc tgatagacgg tttttcgccc tttgacgttg gagtccacgt tctttaatag   4260

tggactcttg ttccaaactg gaacaacact caaccctatc tcggtctatt cttttgattt   4320

ataagggatt ttgccgattt cggcctattg gttaaaaaaa tgagctgatt taacaaaaat   4380

ttaacgcgaa ttttaacaaa atattaacgc ttacaatttc gattcgccat tcaggctgcg   4440

caactgttgg gaagggcgat cggtgcgggc ctcttcgcta ttacgccagc tggcgaaagg   4500

gggatgtgct gcaaggcgat taagttgggt aacgccaggg ttttcccagt cacgacgttg   4560

taaaacgacg gccagtgagc gcgcgataag cttgtaatac gactcactat aggg         4614
```

<210> SEQ ID NO 5
<211> LENGTH: 8148
<212> TYPE: DNA
<213> ORGANISM: Artificial
<220> FEATURE:
<223> OTHER INFORMATION: Plasmid

<400> SEQUENCE: 5

```
gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaaat gagctgattt aacaaaaatt    420

taacgcgaat tttaacaaaa tattaacgct tacaatttcc attcgccatt caggctgcgc    480

aactgttggg aagggcgatc ggtgcgggcc tcttcgctat tacgccagct ggcgaaaggg    540

ggatgtgctg caaggcgatt aagttgggta acgccagggt tttcccagtc acgacgttgt    600

aaaacgacgg ccagtgagcg cgcgataagc ttgtaatacg actcactata gggagtagtg    660

aactaccaca atcaaaatgc ttctcaacat tgtcttgata tctaacttag cctgtttagc    720

ttttgcactc ccacttaagg aaggcactag agggtctagg tgcttcctga atggcgaact    780

ggttaaaact gttaacacat caaaggtcgt ttcagaatgc tgtgtgaaag acgacatatc    840

tatcattaaa tcaaatgctg aacattataa atcaggagat cggttggctg ctgtaataaa    900

atattatcgt ttatatcagg tgaaggattg gcattcttgc aatccaattt atgatgacca    960

cggttccttt atgatattag atatagataa tactggcaca ttaatcccta aaatgcatac   1020

atgcagagtt gaatgcgaaa tagcactgaa taaagatact ggcgaagtta tattgaattc   1080

atatcgaatt aaccactacc gaatctcggg cacaatgcat gtatcaggtt ggtttaaaaa   1140

caaaattgag attcctttgg aaaacacatg cgaatccatt gaggtaacat gtggattaaa   1200

aacacttaat tttcatgcat gtttccatac ccataagtca tgcacccgct attttaaagg   1260

atcaatcctg ccggaattga tgatcgaatc attttgtacg aatcttgaat taatactgct   1320

agtaactttc atattagttg ggtctgtcat gatgatgata ttgacgaaaa catatatagt   1380

atatgtgttc attcctatat tttatccatt tgtgaaatta tatgcttata tgtacaacaa   1440

atattttaaa ttgtgtaaaa attgcctgtt agcagtacat ccctttacaa attgcccatc   1500

gacatgcatc tgtggaatga tttacactac cactgaatca ctcaaattgc atcgcatgtg   1560

taacaattgt tctggctata aagcattgcc gaaaacaagg aaattgtgta aaagtaaaat   1620

atccaatata gtgctatgtg tgataacatc actgatattt ttctcattta tcacacctat   1680

atcgagtcaa tgtatcgata tagaaaaact gccagacgag tatattacat gtaaaagaga   1740

gctagctaat atcaaaagct tgacaattga tgacacatat agctttatat attcctgtac   1800

atgcataatt gtgttaatat tacttaaaaa ggcagcaaag tatatcttgt actgcaactg   1860

cagcttttgt ggtatggtac atgaacgacg tggattgaag ataatggaca actttacaaa   1920

caagtgccta agttgtgtat gcgcagaaaa caagggctta acaattcaca gagcctctga   1980

gaaatgtctg ttcaaatttg aatcaagtta taataggacc gggttgataa tctttatgct   2040

tctgttagtc ccaacaattg taatgacgca agaaactagt attaactgca aaaacattca   2100
```

-continued

```
atcaactcag cttacaatag agcacctgag taagtgcatg gcattttatc aaaataaaac   2160
aagctcacca gttgtaatca atgaaataat ttcagatgct tcagtagacg aacaagaatt   2220
aataaaaagt ttaaacttga actgtaatgt catagatagg tttatttccg aatctagtgt   2280
tattgagact caagtttatt atgagtatat aaaatcacag ttgtgccctc tccaagtgca   2340
tgatattttc actatcaatt cagcaagtaa catacaatgg aaagcactgg cccgaagttt   2400
caccttagga gtgtgcaata cgaatcctca taaacatata tgtagatgct tggagtctat   2460
gcaaatgtgc acatcaacca agacagacca cgctagggaa atgtcaatat attatgatgg   2520
tcatccagat cgctttgagc atgacatgaa aataatattg aatataatga gatatatagt   2580
ccctggatta ggtcgagtct tgcttgatca aatcaaacaa acaaaagact accaagcttt   2640
acgccacata caaggtaagc tttctcctaa atcgcagtca aatttacaac ttaaaggatt   2700
tctggaattt gttgatttta tccttggtgc aaacgtgaca atagaaaaaa cccctcaaac   2760
attaactaca ttatctttga taaaaggagc ccacagaaac ttggatcaaa aagatccagg   2820
tccaacacca atactggtat gcaaatcacc acaaaaagtg gtatgctact caccacgtgg   2880
tgtcacacac ccaggagatt atatatcatg caaatctaag atgtataagt ggccatcttt   2940
aggggtatac aaacataata gagaccagca acaagcctgc agcagtgaca cacattgcct   3000
agagatgttt gaaccagcag aaagaacaat aactacaaaa atatgcaaag taagtgatat   3060
gacttattca gaatcgccat atagtactgg aataccatca tgcaacgtga agagatttgg   3120
atcatgtaat gtaaggggtc atcaatggca aattgcagaa tgctcaaatg gcttatttta   3180
ctatgtttca gctaaagccc attcgaaaac taacgatata acactgtact gtttatcagc   3240
aaattgcctg gacttgcgtt atgcattcag atccagtagt tgttcagata tagtatggga   3300
tacaagttat cgaaataaat taacacctaa atctattaat catccagata ttgaaaacta   3360
catagcagcg cttcagtcag atattgcaaa tgatttaact atgcactact ttaaaccatt   3420
aaaaaacctt ccagcaataa ttcctcaata caaaacaatg acattgaatg gggacaaggt   3480
atcaaatggt attagaaata gttatatcga gtcgcacatc cctgcaatta atggtttatc   3540
agcagggatt aatattgcca tgccaaatgg agaaagcctc ttttccatta ttatctatgt   3600
cagaagagta ataaataaag catcgtatcg atttctatat gaaacaggac ccacaattgg   3660
aataaatgcc aagcacgaag aggtatgtac cgggaagtgc ccaagcccaa taccacatca   3720
agatggttgg gtcacattct caaaggaaag atcaagtaat tggggctgtg aagaatgggg   3780
ttgcttggca ataaatgatg gttgtttata tgggtcatgt caagacataa taaggcctga   3840
atataagata tacaagaagt ctagtattga acaaaaggat gttgaagttt gtataaccat   3900
ggcccatgaa tcattctgca gtaccgttga tgttctccaa cctttaatta gcgacaggat   3960
acaattagat atccaaacga ttcaaatgga ctctatgcca aatataattg cagtcaagaa   4020
tgggaaagtt tatgttggag atatcaatga cttaggttcg acagcaaaga aatgtggctc   4080
agtccaatta tattctgaag ggatcattgg atcgggaacc ccaaaatttg attatgtttg   4140
ccatgcattc aatcgtaaag atgtcatcct tcgaagatgc tttgataact catatcagtc   4200
ttgtcttctc ttggaacaag ataatacatt aactattgct tctaccagtc atatggaagt   4260
gcataaaaaa gtttcaagcg tgggtacaat caattataaa attatgttag ggatttttga   4320
ctacaatgca tattcaacac aagcaacagt cacaatagat gagatcaggt gtggtggttg   4380
ttatggctgc cctgaaggaa tggcttgcgc actcaaattg agtaccaata ccatcgggag   4440
ttgttcaata aaaagtaact gcgatacata cattaaaata atagcagtcg atccgatgca   4500
```

-continued

```
gagcgagtat tccattaagt taaactgccc actagcaaca gagacagttt cagtaagtgt   4560
gtgctcagct tctgcttaca caaaaccttc aatatctaaa aatcaaccaa aaattgtttt   4620
gaattcctta gatgaaacat cttacatcga gcaacatgat aaaaagtgtt ctacatggct   4680
ttgcagagtt tataaagaag ggattagcgt aatatttcag cctctatttg gcaacctatc   4740
tttctattgg agactgacaa tatatataat aatctctttg attatgctaa ttctgtttct   4800
atacatatta ataccactgt gcaaacggct aaaaggttta ttggaataca atgagagaat   4860
ataccaaatg gaaaataaat ttaagtgata agccttataa caatgagcaa ttataaatga   4920
ataaataaaa acaataaaag ataaacaaat aacaacatat atatgtggtt acacatatat   4980
atgtaattat tcagctgaga agtttttcat gtggtagaac actactgggt cggcatggca   5040
tctccacctc ctcgcggtcc gacctgggca tccgaaggag gacgcacgtc cactcggatg   5100
gctaagggag gggcggggat ccggctgcta acaaagcccg aaaggaagct gagttggctg   5160
ctgccaccgc tgagcaataa ctagcataac cccttggggc ctctaaacgg gtcttgaggg   5220
gttttttgct gaaaggagga actatatccg gatccactag ttctagagcg gccgccaccg   5280
cggtggagct ccagcttttg ttccctttag tgagggttaa ttgcgcgctt ggcgtaatca   5340
tggtcatagc tgtttcctgt gtgaaattgt tatccgctca caattccaca caacatacga   5400
gccggaagca taaagtgtaa agcctggggt gcctaatgag tgagctaact cacattaatt   5460
gcgttgcgct cactgcccgc tttccagtcg ggaaacctgt cgtgccagct gcattaatga   5520
atcggccaac gcgcggggag aggcggtttg cgtattgggc gctcttccgc ttcctcgctc   5580
actgactcgc tgcgctcggt cgttcggctg cggcgagcgg tatcagctca ctcaaaggcg   5640
gtaatacggt tatccacaga atcaggggat aacgcaggaa agaacatgtg agcaaaaggc   5700
cagcaaaagg ccaggaaccg taaaaaggcc gcgttgctgg cgtttttcca taggctccgc   5760
ccccctgacg agcatcacaa aaatcgacgc tcaagtcaga ggtggcgaaa cccgacagga   5820
ctataaagat accaggcgtt tccccctgga agctccctcg tgcgctctcc tgttccgacc   5880
ctgccgctta ccggatacct gtccgccttt ctcccttcgg gaagcgtggc gctttctcat   5940
agctcacgct gtaggtatct cagttcggtg taggtcgttc gctccaagct gggctgtgtg   6000
cacgaacccc ccgttcagcc cgaccgctgc gccttatccg gtaactatcg tcttgagtcc   6060
aacccggtaa gacacgactt atcgccactg gcagcagcca ctggtaacag gattagcaga   6120
gcgaggtatg taggcggtgc tacagagttc ttgaagtggt ggcctaacta cggctacact   6180
agaaggacag tatttggtat ctgcgctctg ctgaagccag ttaccttcgg aaaaagagtt   6240
ggtagctctt gatccggcaa acaaaccacc gctggtagcg gtggtttttt tgtttgcaag   6300
cagcagatta cgcgcagaaa aaaaggatct caagaagatc ctttgatctt ttctacgggg   6360
tctgacgctc agtggaacga aaactcacgt taagggattt tggtcatgag attatcaaaa   6420
aggatcttca cctagatcct tttaaattaa aaatgaagtt ttaaatcaat ctaaagtata   6480
tatgagtaaa cttggtctga cagttaccaa tgcttaatca gtgaggcacc tatctcagcg   6540
atctgtctat ttcgttcatc catagttgcc tgactccccg tcgtgtagat aactacgata   6600
cgggagggct taccatctgg ccccagtgct gcaatgatac cgcgagaccc acgctcaccg   6660
gctccagatt tatcagcaat aaaccagcca gccggaaggg ccgagcgcag aagtggtcct   6720
gcaactttat ccgcctccat ccagtctatt aattgttgcc gggaagctag agtaagtagt   6780
tcgccagtta atagtttgcg caacgttgtt gccattgcta caggcatcgt ggtgtcacgc   6840
tcgtcgtttg gtatggcttc attcagctcc ggttcccaac gatcaaggcg agttacatga   6900
```

-continued tcccccatgt tgtgcaaaaa agcggttagc tccttcggtc ctccgatcgt tgtcagaagt 6960
aagttggccg cagtgttatc actcatggtt atggcagcac tgcataattc tcttactgtc 7020
atgccatccg taagatgctt ttctgtgact ggtgagtact caaccaagtc attctgagaa 7080
tagtgtatgc ggcgaccgag ttgctcttgc ccggcgtcaa tacgggataa taccgcgcca 7140
catagcagaa ctttaaaagt gctcatcatt ggaaaacgtt cttcggggcg aaaactctca 7200
aggatcttac cgctgttgag atccagttcg atgtaaccca ctcgtgcacc caactgatct 7260
tcagcatctt ttactttcac cagcgtttct gggtgagcaa aaacaggaag gcaaaatgcc 7320
gcaaaaaagg gaataagggc gacacggaaa tgttgaatac tcatactctt cctttttcaa 7380
tattattgaa gcatttatca gggttattgt ctcatgagcg gatacatatt tgaatgtatt 7440
tagaaaaata aacaaatagg ggttccgcgc acatttcccc gaaaagtgcc acctggacgc 7500
gccctgtagc ggcgcattaa gcgcggcggg tgtggtggtt acgcgcagcg tgaccgctac 7560
acttgccagc gccctagcgc ccgctccttt cgctttcttc ccttcctttc tcgccacgtt 7620
cgccggcttt ccccgtcaag ctctaaatcg ggggctccct ttagggttcc gatttagtgc 7680
tttacggcac ctcgacccca aaaaacttga ttagggtgat ggttcacgta gtgggccatc 7740
gccctgatag acggtttttc gccctttgac gttggagtcc acgttcttta atagtggact 7800
cttgttccaa actggaacaa cactcaaccc tatctcggtc tattcttttg atttataagg 7860
gattttgccg atttcggcct attggttaaa aaatgagct gatttaacaa aaatttaacg 7920
cgaattttaa caaaatatta acgcttacaa tttcgattcg ccattcaggc tgcgcaactg 7980
ttgggaaggg cgatcggtgc gggcctcttc gctattacgc cagctggcga aagggggatg 8040
tgctgcaagg cgattaagtt gggtaacgcc agggttttcc cagtcacgac gttgtaaaac 8100
gacggccagt gagcgcgcga taagcttgta atacgactca ctataggg 8148

<210> SEQ ID NO 6
<211> LENGTH: 10657
<212> TYPE: DNA
<213> ORGANISM: Artificial
<220> FEATURE:
<223> OTHER INFORMATION: Plasmid

<400> SEQUENCE: 6
gacgcgccct gtagcggcgc attaagcgcg gcgggtgtgg tggttacgcg cagcgtgacc 60
gctacacttg ccagcgccct agcgcccgct cctttcgctt tcttcccttc ctttctcgcc 120
acgttcgccg gctttccccg tcaagctcta aatcgggggc tccctttagg gttccgattt 180
agtgctttac ggcacctcga ccccaaaaaa cttgattagg gtgatggttc acgtagtggg 240
ccatcgccct gatagacggt ttttcgccct ttgacgttgg agtccacgtt ctttaatagt 300
ggactcttgt tccaaactgg aacaacactc aaccctatct cggtctattc ttttgattta 360
taagggattt tgccgatttc ggcctattgg ttaaaaaaat gagctgattt aacaaaaatt 420
taacgcgaat tttaacaaaa tattaacgct tacaatttcc attcgccatt caggctgcgc 480
aactgttggg aagggcgatc ggtgcgggcc tcttcgctat tacgccagct ggcgaaaggg 540
ggatgtgctg caaggcgatt aagttgggta acgccagggt tttcccagtc acgacgttgt 600
aaaacgacgg ccagtgagcg cgcgataagc ttgtaatacg actcactata gggagtagtg 660 taccccctaat tacaatcact atggagacat acaagattaa catttttaga gataggatca 720
accagtgtcg aagtgctgaa gaagccaaag acattgttgc tgatcttctc atggctagac 780
atgactactt tggtagagag gtatgttatt acctggatat cgaattccgg caggatgttc 840

-continued

```
cagcttacga catacttctt gaatttctgc cagctggcac tgctttcaac attcgcaatt    900
gtacaccaga caattttatc attcacaatg gcaagcttta tatcattgac tataaagtat    960
caactgatca tgcatatggt caaaaaactt atgaaaagta cacccagatc tttggagacg   1020
cattgtcaga attgccgttt gattttgaag ttgtgatcat ccgtgctgac cctctgcgag   1080
atactatcca tgttaattca aatcaattct tggaaatatt tgggccgctc aacataaacc   1140
ttgattttac ttggttcttt aatttgcgat ccctgatata tgagaaatat aaggatgacg   1200
acagattcct agaaattgtg aatcaaggtg aatttacgat gactggaccc tggattgatg   1260
aggatacccc ggagctctat tcacaccctg tctttttgga attctatgat tctttagatg   1320
agatggctaa actgacattc catgagtcta tgacatttga tgcaactcgc ggtgagaaat   1380
ggaatcaaaa tctacaaaag gttataaata gatatggcaa tgattataac atttttgtga   1440
aagaggccgc tgcaggaatc tttagatgtg aagggaacta cccaaaacca aatcatgatg   1500
aaatcacaat cggttggaat caaatggttc aaagagtgag tactgagaga aacctgactc   1560
aagatgtcag caagcaaaaa ccatctattc atttcatatg ggtcaacct gacgaaacat    1620
caaatgcgac aacaccaaaa ctaatcaaga ttgcaaaagc actccaaaat atttctggcg   1680
agtctacata tataagcgca ttcagagcat tgggtatgct tatggacttt tctgagaaca   1740
cagctttata tgaagcacac actagcaaac taaaaagtat ggcaagacag acatcgaaaa   1800
gaattgatac taaactggaa ccaatcaaaa taggcacggc gacaatttat tgggaacagc   1860
agtttaaact ggatactgaa ataatgaata caaaagacaa atcacatttg ctaaaagatt   1920
ttcttggcat agggggtcac gtgcaatttt caaaaaagac cattgacgat ttggatactg   1980
acaaacctac tatattagat ttcaacaaaa aggaagtcat tgatttttgc aaattccagt   2040
atgaaaatgt aaagaaaata ctatccggag ataataatct agagcgtata ggatgttatt   2100
tagaagaata tggtgcaaat attgcatcat gttcaaagga tacatgggat cagattaacc   2160
agatagggaa gtcaaattac tgggcttgta ttaaagattt ttcagtcttg atgaaaaata   2220
tgttggcagt ttctcaatat aataggcaca atacttttcg tgtagtgtgt tgtgcaaaca   2280
ataatctgtt tgggtttgta atgccttctt ctgatattaa agcaaagcga tccacacttg   2340
tttacttctt agctgtgttg cattctactc ctcagaatgt gatgcaccac ggtgcattgc   2400
atgcgacatt taaaactggt tcaaaatacc ttagtatctc taaaggaatg cgtttagata   2460
aagaacgatg tcaacgcata gttagttcac cgggactttt tatgttgact acattgatgt   2520
ttgcaggaga caatccgaca ctcaatttga ctgatgtcat gaattttaca ttccacactt   2580
ccctgtctat aaccaaagct atgctgtcat tgacagaacc atcaagatat atgataatga   2640
attcattagc catatccagt catgttagag attatatagc agaaaaattt ggcccttata   2700
caaagaccag cttctctgta gtaatggcaa acttgattaa aaggggatgt tatatggcat   2760
ataatcaaag agataaagta gacatgagga atatctgcct aacagattat gaaataactc   2820
aaaaaggtgt gagagataac agagacctat catcaatctg gtttgaaggc tatgtatcac   2880
taaaagaata tattaaccaa atatatctac cattttactt caattcaaaa ggtttgcatg   2940
aaaagcatca tgttatgata gatctggcta agacaatctt agatatagaa agggaccaga   3000
gattaaatat cccaggaata tggtctacaa cacctagaaa acaaactgca aatttaaata   3060
taactatcta tgcagttgca aaaaatctaa taatggacac tgctagacat aattatatta   3120
gatcacggat agaaaacaca aacaacttaa atagatcgat atgcactatt tctacattca   3180
ccagctctaa atcatgtatt aaagtaggcg actttgagaa agaaaaaagc tcagcaacaa   3240
```

-continued aaaaggctgc agattgcatg tcaaaagaga taaagaagta tacaattgca aacccagaat 3300
ttgttgatga agagttacta aatgcaacta taagacattc acgctatgaa gacttaaaaa 3360
aagcaatccc gaattatatt gacattatgt caactaaagt atttgattct ctgtaccaga 3420
aaataaaaag gaaggagata gatgataaac ccactgtgta tcatatactc tctgctatga 3480
agaatcacac agattttaag tttacattct ttaacaaagg ccaaaaaaca gcaaaggata 3540
gggaaatatt cgtaggcgaa tttgaggcaa aaatgtgctt gtatttagtg gagaggatat 3600
ctaaagaacg ctgtaagttg aatccagatg agatgattag tgaaccaggc gattctaaat 3660
tgaaaaaatt agaagagctt gcagagtctg aaatacgatt cacagcagca actatgaaac 3720
agatcaaaga acgctattta gcagaaatgg gagaagcaag ccatatgatc gcatataaac 3780
cacattctgt taagattgaa atcaatgcag acatgtcaaa atggagtgcc caagatgttt 3840
tattcaaata tttctggttg tttgcattag atcccgcact ttatctgcaa gaaaaagaaa 3900
ggatattgta cttcctatgc aattatatgc aaaaaaagct aattctgcct gatgaaatgc 3960
tctgtagcat ccttgaccaa cgtatcaaac atgaggatga tataatatat gaaatgacca 4020
atggcttatc gcaaaattgg gtcaatatta aacggaactg gctgcagggg aatctcaatt 4080
acacaagtag ctacctacat tcatgttcta tgaatgttta taaggatatt ctaaagagag 4140
cagccacttt actagaaggg gaagttttag tcaattctat ggttcattct gatgacaatc 4200
acacttcaat agtgatgatc caagataaat tagatgatga tattgttatt gaattttctg 4260
caaaactatt tgaaaaaata tgtctaactt ttggaaatca agcaaatatg aagaagacat 4320
atataacaaa tttcataaag gagttcgttt cactttttaa tatttatggt gagccatttt 4380
ctgtttatgg tcgctttatt ttgacatctg ttggcgattg tgcttttctt ggaccatatg 4440
aggatgttgc cagtaggttg tctgcaacgc agacagcaat taagcatgga gcacctccat 4500
cacttgcatg gactgctatt gcattaactc agtggataac acatagcaca tataacatgc 4560
ttccaggtca aatcaatgat cctacttcat ctttacctag tcatgataga tttgagctgc 4620
ctatagaatt gtgtggctta ataaattcag aattacccac tatagctata gcaggtttgg 4680
aagcagataa tctaagttat ttagttaggt tatcaaaaag aatgtcccct atacatcttt 4740
gccgtgaacc aatccagcat caatatgaga atatacatac atgggatata agtaaactga 4800
cacaatgtga tattttcaga cttaagcttt taagatacat gacgttagac tcaactatgt 4860
catctgatga tggaatgggc gaaactagtg aaatgagatc taggtctctt ctgacaccaa 4920
gaaaattcac tactgcaagt tcgttatcta gattgcattc atatgctgat tatcaaaaaa 4980
caatacaaga ccaacagaaa attgaagaat tatttgaata ttttatagcc aaccctcaac 5040
tattggttac aaaaggtgag acttgtgaag agttctgtat gtctgtattg ttcagataca 5100
acagtcgtaa atttaaagaa tcattgtcta ttcaaaaccc agctcagctc ttcatagaac 5160
aagtattgtt tgcaaataaa ccaatgatag actatacaag tattcatgat aggttgtttg 5220
gtatacaaga tgacccaaat ataaatgatg ctacatgtat tattggcaag aagacttttg 5280
ttgaaacata tcagcaaata aaaattgatg tagaaaaatt tacacttgat gtagaggata 5340
taaagacgat atatagcttc tgtataatga acgaccctat attagttgct tgtgcaaaca 5400
acttgttaat ttcaatacag ggagtggaga tgcaacgatt gggtatgaca tgctgttata 5460
tgccggagat taagagcctt aaagtaattt atcatagtcc tgctctcgta ttacgtgctt 5520
atgtaacaga taactatgag caaaaaggga tggagccaga tgaaatgcgg agagatatat 5580
atcatttaga agaatttata gagaagacaa aattgaggac aaatatgcaa gggagaattg 5640

-continued

```
caaataatga aattaagtta atgaagcgag atttgaaatt tgaagtgcag gaattgacta   5700
aattctatca gatctgttat gaatatgtga aatcaacaga acacaaaatt aaaatattca   5760
tccttccaaa aaaggcttac actcccattg atttctgctc attagtaaca ggtaatctga   5820
tatcagacaa caaatggatg gttgttcact atttaaaaca aataactgtc ccagcaaaga   5880
aggcacaaat agccacatct atagatctgg aaatacaaat agcctacgaa tgtttcaggc   5940
taattgcaca ttttgctgat atgttcctaa atgatgactc caaaaaagct tatattaatg   6000
caattattaa cacatataca tacaaggatg ttcaagtatc cagtctctac aagaaaatca   6060
aaaattcgag actacgttca aaaattatac cattattata tcacctgggc gatttgcaac   6120
aaatagacgt tgacagattt gatgcagaaa aagcagaaga gcagatcaca tggaataact   6180
ggcaaacatc tcgagaattt actactggtc caattgatct atcaatcaaa ggttatggac   6240
ggtcaataag gatcgtaggt gaggacaaca agcttacagc tgcagaaatg caattgtcaa   6300
gagtgagaag tgatatagta tcaaggcatg gacaggcttt attgaacaaa cctcatgggc   6360
taaaattaga gaaaatggaa ccagtgactg atctaaatcc taaattatgg tatattgcat   6420
accaattgcg tgagaaaaag cggtatcact atggggtctt tagtacatct tatatagaag   6480
agcataactc aaggatagaa gcatctcgga tacgtaagac taataaatgg ataccagttt   6540
gccctattgc tatatcaaaa caatcatctg atggaaagcc tagtcttgca aaaatcccta   6600
tgttaaatat tggggagatt aaatttacaa aactacagat tgcagtagat gatcatgcaa   6660
tgattaggaa agccccattt agtaagatgg tgttctttga tggcccaccc atacagagcg   6720
gtggcattga cattggaaag cttatgaaga accaaaatat tctcaatttg aggttagata   6780
atatacagag tataacatta ttagatttgt gccgcatatt ttcatgccga gggtctaaag   6840
tggatcaaga tgcatttgaa ttcttatctg atgaaccttt ggatgaagat gttattgatg   6900
aattagatag ctcacctgca ttagtggtat cttacacaaa gaaatcaacc aaatccaata   6960
gtttcaaaaa tgttatagtt agagcattga taagagaatg tgatatattt gaagatataa   7020
tggacataac agacgatgga ttcacatctg atagcaatct agaggtgtta gaaaacttaa   7080
catggatttt aaatatgctc gcaacaaatc agtggtctac agaactgtta gcatgcatac   7140
acatgtgttt atatcgcaat gagatggatc atatctatca caattttcaa gttccagaaa   7200
tatttgtcga caatccaatc tcattaaatg taaagtggga tgaagtaatt atgttcttaa   7260
acatactgcg agacagagat tacaaatttg agccatgggt gtctatactg aatcattcct   7320
taactaaagc tatagagtat gcttacaaaa agatggaaga ggagaggaag cagaaatcaa   7380
caggcatcaa caaattctta aagggtaaaa aaatgggtgg cagatcaaag tttgatttcc   7440
agtagcttga tcttaaataa tacataatct ttgccccaaa tctgtattat ataaataatt   7500
ctaaagtagt ttcatgtaat taggggcaca ctactgggtc ggcatggcat ctccacctcc   7560
tcgcggtccg acctgggcat ccgaaggagg acgcacgtcc actcggatgg ctaagggagg   7620
ggcggggatc cggctgctaa caaagcccga aaggaagctg agttggctgc tgccaccgct   7680
gagcaataac tagcataacc ccttggggcc tctaaacggg tcttgagggg ttttttgctg   7740
aaaggaggaa ctatatccgg atccactagt tctagagcgg ccgccaccgc ggtggagctc   7800
cagcttttgt tccctttagt gagggttaat tgcgcgcttg gcgtaatcat ggtcatagct   7860
gtttcctgtg tgaaattgtt atccgctcac aattccacac aacatacgag ccggaagcat   7920
aaagtgtaaa gcctggggtg cctaatgagt gagctaactc acattaattg cgttgcgctc   7980
actgcccgct ttccagtcgg gaaacctgtc gtgccagctg cattaatgaa tcggccaacg   8040
```

-continued

```
cgcggggaga ggcggtttgc gtattgggcg ctcttccgct tcctcgctca ctgactcgct   8100
gcgctcggtc gttcggctgc ggcgagcggt atcagctcac tcaaaggcgg taatacggtt   8160
atccacagaa tcaggggata acgcaggaaa gaacatgtga gcaaaaggcc agcaaaaggc   8220
caggaaccgt aaaaaggccg cgttgctggc gtttttccat aggctccgcc cccctgacga   8280
gcatcacaaa aatcgacgct caagtcagag gtggcgaaac ccgacaggac tataaagata   8340
ccaggcgttt ccccctggaa gctccctcgt gcgctctcct gttccgaccc tgccgcttac   8400
cggatacctg tccgcctttc tcccttcggg aagcgtggcg ctttctcata gctcacgctg   8460
taggtatctc agttcggtgt aggtcgttcg ctccaagctg ggctgtgtgc acgaaccccc   8520
cgttcagccc gaccgctgcg ccttatccgg taactatcgt cttgagtcca acccggtaag   8580
acacgactta tcgccactgg cagcagccac tggtaacagg attagcagag cgaggtatgt   8640
aggcggtgct acagagttct tgaagtggtg gcctaactac ggctacacta gaaggacagt   8700
atttggtatc tgcgctctgc tgaagccagt taccttcgga aaaagagttg gtagctcttg   8760
atccggcaaa caaaccaccg ctggtagcgg tggttttttt gtttgcaagc agcagattac   8820
gcgcagaaaa aaaggatctc aagaagatcc tttgatcttt tctacggggt ctgacgctca   8880
gtggaacgaa aactcacgtt aagggatttt ggtcatgaga ttatcaaaaa ggatcttcac   8940
ctagatcctt ttaaattaaa aatgaagttt taaatcaatc taaagtatat atgagtaaac   9000
ttggtctgac agttaccaat gcttaatcag tgaggcacct atctcagcga tctgtctatt   9060
tcgttcatcc atagttgcct gactccccgt cgtgtagata actacgatac gggagggctt   9120
accatctggc cccagtgctg caatgatacc gcgagaccca cgctcaccgg ctccagattt   9180
atcagcaata aaccagccag ccggaagggc cgagcgcaga agtggtcctg caactttatc   9240
cgcctccatc cagtctatta attgttgccg ggaagctaga gtaagtagtt cgccagttaa   9300
tagtttgcgc aacgttgttg ccattgctac aggcatcgtg gtgtcacgct cgtcgtttgg   9360
tatggcttca ttcagctccg gttcccaacg atcaaggcga gttacatgat cccccatgtt   9420
gtgcaaaaaa gcggttagct ccttcggtcc tccgatcgtt gtcagaagta agttggccgc   9480
agtgttatca ctcatggtta tggcagcact gcataattct cttactgtca tgccatccgt   9540
aagatgcttt tctgtgactg gtgagtactc aaccaagtca ttctgagaat agtgtatgcg   9600
gcgaccgagt tgctcttgcc cggcgtcaat acgggataat accgcgccac atagcagaac   9660
tttaaaagtg ctcatcattg gaaaacgttc ttcggggcga aaactctcaa ggatcttacc   9720
gctgttgaga tccagttcga tgtaacccac tcgtgcaccc aactgatctt cagcatcttt   9780
tactttcacc agcgtttctg ggtgagcaaa aacaggaagg caaaatgccg caaaaaaggg   9840
aataagggcg acacggaaat gttgaatact catactcttc ctttttcaat attattgaag   9900
catttatcag ggttattgtc tcatgagcgg atacatattt gaatgtattt agaaaaataa   9960
acaaataggg gttccgcgca catttccccg aaaagtgcca cctggacgcg ccctgtagcg  10020
gcgcattaag cgcggcgggt gtggtggtta cgcgcagcgt gaccgctaca cttgccagcg  10080
ccctagcgcc cgctcctttc gctttcttcc cttcctttct cgccacgttc gccggctttc  10140
cccgtcaagc tctaaatcgg gggctccctt tagggttccg atttagtgct ttacggcacc  10200
tcgaccccaa aaaacttgat tagggtgatg gttcacgtag tgggccatcg ccctgataga  10260
cggtttttcg ccctttgacg ttggagtcca cgttctttaa tagtggactc ttgttccaaa  10320
ctggaacaac actcaaccct atctcggtct attcttttga tttataaggg attttgccga  10380
tttcggccta ttggttaaaa aaatgagctg atttaacaaa aatttaacgc gaattttaac  10440
```

```
aaaatattaa cgcttacaat ttcgattcgc cattcaggct gcgcaactgt tgggaagggc  10500

gatcggtgcg ggcctcttcg ctattacgcc agctggcgaa agggggatgt gctgcaaggc  10560

gattaagttg ggtaacgcca gggttttccc agtcacgacg ttgtaaaacg acggccagtg  10620

agcgcgcgat aagcttgtaa tacgactcac tataggg                           10657
```

```
<210> SEQ ID NO 7
<211> LENGTH: 839
<212> TYPE: DNA
<213> ORGANISM: Schmallenberg virus

<400> SEQUENCE: 7

agtagtgaac tccactatta actacagaaa tatgtcaagc caattcattt ttgaagatgt     60

accacaacgg aatgcagcta catttaaccc ggaggtcggg tatgtggcat ttattggtaa    120

gtatgggcaa caactcaact tcggtgttgc tagagtcttc ttcctcaacc agaagaaggc    180

caagatggtc ctacataaga cggcacaacc aagtgtcgat cttacttttg gtggggtcaa    240

atttacagtg gttaataacc attttcccca atatgtctca aatcctgtgc cagacaatgc    300

cattacactt cacaggatgt caggatatct agcacgttgg attgctgata catgcaaggc    360

tagtgtcctc aaactagctg aagctagtgc tcagattgtc atgccccttg ctgaggttaa    420

gggatgcacc tgggccgatg gttatacaat gtatcttgga tttgcacctg gggccgaaat    480

gttccttgat gcttttgact tctatccact agttattgaa atgcataggg tcctcaagga    540

caatatggat gtaaatttta tgaaaaaagt cctccgccaa cgctatggaa caatgactgc    600

tgaagaatgg atgactcaga aaataacaga aataaaagct gcttttaatt ctgttggaca    660

gcttgcctgg gccaaatctg gattctctcc tgctgctaga accttcttgc agcaattcgg    720

tatcaacatc taaacctctt catcacagat cttcaatttc cgtgcaatat gtctatgtat    780

tgcacaccat tatactgcaa ggcttctgtt aagatagtta ataagtggag aacactact     839
```

```
<210> SEQ ID NO 8
<211> LENGTH: 3991
<212> TYPE: DNA
<213> ORGANISM: Artificial
<220> FEATURE:
<223> OTHER INFORMATION: Plasmid

<400> SEQUENCE: 8

aattctaata cgactcacta tagagtagtg aactccacta ttaactacag aaatatgtca     60

agccaattca tttttgaaga tgtaccacaa cggaatgcag ctacatttaa cccggaggtc    120

gggtatgtgg catttattgg taagtatggg caacaactca acttcggtgt tgctagagtc    180

ttcttcctca accagaagaa ggccaagatg gtcctacata agacggcaca accaagtgtc    240

gatcttactt ttggtggggt caaatttaca gtggttaata accattttcc ccaatatgtc    300

tcaaatcctg tgccagacaa tgccattaca cttcacagga tgtcaggata tctagcacgt    360

tggattgctg atacatgcaa ggctagtgtc ctcaaactag ctgaagctag tgctcagatt    420

gtcatgcccc ttgctgaggt taagggatgc acctgggccg atggttatac aatgtatctt    480

ggatttgcac ctggggccga aatgttcctt gatgcttttg acttctatcc actagttatt    540

gaaatgcata gggtcctcaa ggacaatatg gatgtaaatt ttatgaaaaa agtcctccgc    600

caacgctatg gaacaatgac tgctgaagaa tggatgactc agaaaataac agaaataaaa    660

gctgctttta attctgttgg acagcttgcc tgggccaaat ctggattctc tcctgctgct    720

agaaccttct tgcagcaatt cggtatcaac atctaaacct cttcatcaca gatcttcaat    780
```

-continued

```
ttccgtgcaa tatgtctatg tattgcacac cattatactg caaggcttct gttaagatag    840
ttaataagtg gagaacacta ctgggtcggc atggcatctc cacctcctcg cggtccgacc    900
tgggcatccg aaggaggacg cacgtccact cggatggcta agggagggat ccggctgcta    960
acaaagcccg aaaggaagct gagttggctg ctgccaccgc tgagcaataa ctagcataac   1020
cccttggggc ctctaaacgg gtcttgaggg gttttttgct gaaaggagga actatatccg   1080
gatggggatc ctctagagtc gacctgcagg catgcaagct tggcactggc cgtcgtttta   1140
caacgtcgtg actgggaaaa ccctggcgtt acccaactta atcgccttgc agcacatccc   1200
cctttcgcca gctggcgtaa tagcgaagag gcccgcaccg atcgcccttc ccaacagttg   1260
cgcagcctga atggcgaatg gcgcctgatg cggtattttc tccttacgca tctgtgcggt   1320
atttcacacc gcatacgtca aagcaaccat agtacgcgcc ctgtagcggc gcattaagcg   1380
cggcgggtgt ggtggttacg cgcagcgtga ccgctacact tgccagcgcc ctagcgcccg   1440
ctcctttcgc tttcttccct tcctttctcg ccacgttcgc cggctttccc cgtcaagctc   1500
taaatcgggg gctcccttta gggttccgat ttagtgcttt acggcacctc gaccccaaaa   1560
aacttgattt gggtgatggt tcacgtagtg ggccatcgcc ctgatagacg gtttttcgcc   1620
ctttgacgtt ggagtccacg ttctttaata gtggactctt gttccaaact ggaacaacac   1680
tcaaccctat ctcggctat tcttttgatt tataagggat tttgccgatt tcggcctatt   1740
ggttaaaaaa tgagctgatt taacaaaaat ttaacgcgaa ttttaacaaa atattaacgt   1800
ttacaatttt atggtgcact ctcagtacaa tctgctctga tgccgcatag ttaagccagc   1860
cccgacaccc gccaacaccc gctgacgcgc cctgacgggc ttgtctgctc ccggcatccg   1920
cttacagaca agctgtgacc gtgtccggga gctgcatgtg tcagaggttt tcaccgtcat   1980
caccgaaacg cgccagacga aagggcctcg tgatacgcct atttttatag gttaatgtca   2040
tgataataat ggtttcttag acgtcaggtg gcacttttcg gggaaatgtg cgcggaaccc   2100
ctatttgttt atttttctaa atacattcaa atatgtatcc gctcatgaga caataaccct   2160
gataaatgct tcaataatat tgaaaaagga agagtatgag tattcaacat ttccgtgtcg   2220
cccttattcc cttttttgcg gcattttgcc ttcctgtttt tgctcaccca gaaacgctgg   2280
tgaaagtaaa agatgctgaa gatcagttgg gtgcacgagt gggttacatc gaactggatc   2340
tcaacagcgg taagatcctt gagagttttc gccccgaaga acgttttcca atgatgagca   2400
cttttaaagt tctgctatgt ggcgcggtat tatcccgtat tgacgccggg caagagcaac   2460
tcggtcgccg catacactat tctcagaatg acttggttga gtactcacca gtcacagaaa   2520
agcatcttac ggatggcatg acagtaagag aattatgcag tgctgccata accatgagtg   2580
ataacactgc ggccaactta cttctgacaa cgatcggagg accgaaggag ctaaccgctt   2640
ttttgcacaa catgggggat catgtaactc gccttgatcg ttgggaaccg gagctgaatg   2700
aagccatacc aaacgacgag cgtgacacca cgatgcctgt agcaatggca acaacgttgc   2760
gcaaactatt aactggcgaa ctacttactc tagcttcccg gcaacaatta atagactgga   2820
tggaggcgga taaagttgca ggaccacttc tgcgctcggc ccttccggct ggctggttta   2880
ttgctgataa atctggagcc ggtgagcgtg ggtctcgcgg tatcattgca gcactggggc   2940
cagatggtaa gccctcccgt atcgtagtta tctacacgac ggggagtcag gcaactatgg   3000
atgaacgaaa tagacagatc gctgagatag gtgcctcact gattaagcat tggtaactgt   3060
cagaccaagt ttactcatat atactttaga ttgatttaaa acttcatttt taatttaaaa   3120
ggatctaggt gaagatcctt tttgataatc tcatgaccaa aatcccttaa cgtgagtttt   3180
```

-continued cgttccactg agcgtcagac cccgtagaaa agatcaaagg atcttcttga gatccttttt 3240
ttctgcgcgt aatctgctgc ttgcaaacaa aaaaaccacc gctaccagcg gtggtttgtt 3300
tgccggatca agagctacca actctttttc cgaaggtaac tggcttcagc agagcgcaga 3360
taccaaatac tgtccttcta gtgtagccgt agttaggcca ccacttcaag aactctgtag 3420
caccgcctac atacctcgct ctgctaatcc tgttaccagt ggctgctgcc agtggcgata 3480
agtcgtgtct taccgggttg gactcaagac gatagttacc ggataaggcg cagcggtcgg 3540
gctgaacggg gggttcgtgc acacagccca gcttggagcg aacgacctac accgaactga 3600
gatacctaca gcgtgagcta tgagaaagcg ccacgcttcc cgaagggaga aaggcggaca 3660
ggtatccggt aagcggcagg gtcggaacag gagagcgcac gagggagctt ccagggggaa 3720
acgcctggta tctttatagt cctgtcgggt ttcgccacct ctgacttgag cgtcgatttt 3780
tgtgatgctc gtcagggggg cggagcctat ggaaaaacgc cagcaacgcg gcctttttac 3840
ggttcctggc cttttgctgg ccttttgctc acatgttctt tcctgcgtta tcccctgatt 3900
ctgtggataa ccgtattacc gcctttgagt gagctgatac cgctcgccgc agccgaacga 3960
ccgagcgcag cgagtcagtg agcgaggaag c 3991

<210> SEQ ID NO 9
<211> LENGTH: 7525
<212> TYPE: DNA
<213> ORGANISM: Artificial
<220> FEATURE:
<223> OTHER INFORMATION: Plasmid

<400> SEQUENCE: 9
aattctaata cgactcacta tagagtagtg aactaccaca atcaaaatgc ttctcaacat 60
tgtcttgata tctaacttag cctgtttagc ttttgcactc ccacttaagg aaggcactag 120
agggtctagg tgcttcctga atggcgaact ggttaaaact gttaacacat caaaggtcgt 180
ttcagaatgc tgtgtgaaag acgacatatc tatcattaaa tcaaatgctg aacattataa 240
atcaggagat cggttggctg ctgtaataaa atattatcgt ttatatcagg tgaaggattg 300
gcattcttgc aatccaattt atgatgacca cggttccttt atgatattag atatagataa 360
tactggcaca ttaatcccta aaatgcatac atgcagagtt gaatgcgaaa tagcactgaa 420
taaagatact ggcgaagtta tattgaattc atatcgaatt aaccactacc gaatctcggg 480
cacaatgcat gtatcaggtt ggtttaaaaa caaaattgag attcctttgg aaaacacatg 540
cgaatccatt gaggtaacat gtggattaaa aacacttaat tttcatgcat gtttccatac 600
ccataagtca tgcacccgct attttaaagg atcaatcctg ccggaattga tgatcgaatc 660
attttgtacg aatcttgaat taatactgct agtaactttc atattagttg ggtctgtcat 720
gatgatgata ttgacgaaaa catatatagt atatgtgttc attcctatat tttatccatt 780
tgtgaaatta tatgcttata tgtacaacaa atattttaaa ttgtgtaaaa attgcctgtt 840
agcagtacat ccctttacaa attgcccatc gacatgcatc tgtggaatga tttacactac 900
cactgaatca ctcaaattgc atcgcatgtg taacaattgt tctggctata aagcattgcc 960
gaaaacaagg aaattgtgta aaagtaaaat atccaatata gtgctatgtg tgataacatc 1020
actgatattt ttctcattta tcacacctat atcgagtcaa tgtatcgata tagaaaaact 1080
gccagacgag tatattacat gtaaaagaga gctagctaat atcaaaagct tgacaattga 1140
tgacacatat agctttatat attcctgtac atgcataatt gtgttaatat tacttaaaaa 1200
ggcagcaaag tatatcttgt actgcaactg cagcttttgt ggtatggtac atgaacgacg 1260

-continued

```
tggattgaag ataatggaca actttacaaa caagtgccta agttgtgtat gcgcagaaaa   1320
caagggctta acaattcaca gagcctctga gaaatgtctg ttcaaatttg aatcaagtta   1380
taataggacc gggttgataa tctttatgct tctgttagtc ccaacaattg taatgacgca   1440
agaaactagt attaactgca aaaacattca atcaactcag cttacaatag agcacctgag   1500
taagtgcatg gcattttatc aaaataaaac aagctcacca gttgtaatca atgaaataat   1560
ttcagatgct tcagtagacg aacaagaatt aataaaaagt ttaaacttga actgtaatgt   1620
catagatagg tttatttccg aatctagtgt tattgagact caagtttatt atgagtatat   1680
aaaatcacag ttgtgccctc tccaagtgca tgatattttc actatcaatt cagcaagtaa   1740
catacaatgg aaagcactgg cccgaagttt caccttagga gtgtgcaata cgaatcctca   1800
taaacatata tgtagatgct tggagtctat gcaaatgtgc acatcaacca agacagacca   1860
cgctagggaa atgtcaatat attatgatgg tcatccagat cgctttgagc atgacatgaa   1920
aataatattg aatataatga gatatatagt ccctggatta ggtcgagtct tgcttgatca   1980
aatcaaacaa acaaaagact accaagcttt acgccacata caaggtaagc tttctcctaa   2040
atcgcagtca aatttacaac ttaaaggatt tctggaattt gttgatttta tccttggtgc   2100
aaacgtgaca atagaaaaaa cccctcaaac attaactaca ttatctttga taaaaggagc   2160
ccacagaaac ttggatcaaa aagatccagg tccaacacca atactggtat gcaaatcacc   2220
acaaaaagtg gtatgctact caccacgtgg tgtcacacac ccaggagatt atatatcatg   2280
caaatctaag atgtataagt ggccatcttt aggggtatac aaacataata gagaccagca   2340
acaagcctgc agcagtgaca cacattgcct agagatgttt gaaccagcag aaagaacaat   2400
aactacaaaa atatgcaaag taagtgatat gacttattca gaatcgccat atagtactgg   2460
aataccatca tgcaacgtga agagatttgg atcatgtaat gtaaggggtc atcaatggca   2520
aattgcagaa tgctcaaatg gcttatttta ctatgtttca gctaaagccc attcgaaaac   2580
taacgatata acactgtact gtttatcagc aaattgcctg gacttgcgtt atgcattcag   2640
atccagtagt tgttcagata tagtatggga tacaagttat cgaaataaat taacacctaa   2700
atctattaat catccagata ttgaaaacta catagcagcg cttcagtcag atattgcaaa   2760
tgatttaact atgcactact ttaaaccatt aaaaaacctt ccagcaataa ttcctcaata   2820
caaaacaatg acattgaatg gggacaaggt atcaaatggt attagaaata gttatatcga   2880
gtcgcacatc cctgcaatta atggtttatc agcagggatt aatattgcca tgccaaatgg   2940
agaaagcctc ttttccatta ttatctatgt cagaagagta ataaataaag catcgtatcg   3000
atttctatat gaaacaggac ccacaattgg aataaatgcc aagcacgaag aggtatgtac   3060
cgggaagtgc ccaagcccaa taccacatca agatggttgg gtcacattct caaaggaaag   3120
atcaagtaat tggggctgtg aagaatgggg ttgcttggca ataaatgatg gttgtttata   3180
tgggtcatgt caagacataa taaggcctga atataagata tacaagaagt ctagtattga   3240
acaaaaggat gttgaagttt gtataaccat ggcccatgaa tcattctgca gtaccgttga   3300
tgttctccaa cctttaatta gcgacaggat acaattagat atccaaacga ttcaaatgga   3360
ctctatgcca aatataattg cagtcaagaa tgggaaagtt tatgttggag atatcaatga   3420
cttaggttcg acagcaaaga aatgtggctc agtccaatta tattctgaag ggatcattgg   3480
atcgggaacc ccaaaatttg attatgtttg ccatgcattc aatcgtaaag atgtcatcct   3540
tcgaagatgc tttgataact catatcagtc ttgtcttctc ttggaacaag ataatacatt   3600
aactattgct tctaccagtc atatggaagt gcataaaaaa gtttcaagcg tgggtacaat   3660
```

-continued

```
caattataaa attatgttag gggattttga ctacaatgca tattcaacac aagcaacagt   3720
cacaatagat gagatcaggt gtggtggttg ttatggctgc cctgaaggaa tggcttgcgc   3780
actcaaattg agtaccaata ccatcgggag ttgttcaata aaaagtaact gcgatacata   3840
cattaaaata atagcagtcg atccgatgca gagcgagtat tccattaagt taaactgccc   3900
actagcaaca gagacagttt cagtaagtgt gtgctcagct tctgcttaca caaaaccttc   3960
aatatctaaa aatcaaccaa aaattgtttt gaattcctta gatgaaacat cttacatcga   4020
gcaacatgat aaaaagtgtt ctacatggct ttgcagagtt tataaagaag ggattagcgt   4080
aatatttcag cctctatttg gcaacctatc tttctattgg agactgacaa tatatataat   4140
aatctctttg attatgctaa ttctgtttct atacatatta ataccactgt gcaaacggct   4200
aaaaggttta ttggaataca atgagagaat ataccaaatg gaaaataaat ttaagtgata   4260
agccttataa caatgagcaa ttataaatga ataaataaaa acaataaaag ataaacaaat   4320
aacaacatat atatgtggtt acacatatat atgtaattat tcagctgaga agtttttcat   4380
gtggtagaac actactgggt cggcatggca tctccacctc ctcgcggtcc gacctgggca   4440
tccgaaggag gacgcacgtc cactcggatg gctaagggag ggatccggct gctaacaaag   4500
cccgaaagga agctgagttg gctgctgcca ccgctgagca ataactagca taaccccttg   4560
gggcctctaa acgggtcttg aggggttttt tgctgaaagg aggaactata tccggatggg   4620
gatcctctag agtcgacctg caggcatgca agcttggcac tggccgtcgt tttacaacgt   4680
cgtgactggg aaaaccctgg cgttacccaa cttaatcgcc ttgcagcaca tccccctttc   4740
gccagctggc gtaatagcga agaggcccgc accgatcgcc cttcccaaca gttgcgcagc   4800
ctgaatggcg aatggcgcct gatgcggtat tttctcctta cgcatctgtg cggtatttca   4860
caccgcatac gtcaaagcaa ccatagtacg cgccctgtag cggcgcatta agcgcggcgg   4920
gtgtggtggt tacgcgcagc gtgaccgcta cacttgccag cgccctagcg cccgctcctt   4980
tcgctttctt cccttccttt ctcgccacgt tcgccggctt tccccgtcaa gctctaaatc   5040
gggggctccc tttagggttc cgatttagtg ctttacggca cctcgacccc aaaaaacttg   5100
atttgggtga tggttcacgt agtgggccat cgccctgata gacggttttt cgccctttga   5160
cgttggagtc cacgttcttt aatagtggac tcttgttcca aactggaaca acactcaacc   5220
ctatctcggg ctattctttt gatttataag ggattttgcc gatttcggcc tattggttaa   5280
aaaatgagct gatttaacaa aaatttaacg cgaattttaa caaaatatta acgtttacaa   5340
ttttatggtg cactctcagt acaatctgct ctgatgccgc atagttaagc cagccccgac   5400
acccgccaac acccgctgac gcgccctgac gggcttgtct gctcccggca tccgcttaca   5460
gacaagctgt gaccgtgtcc gggagctgca tgtgtcagag gttttcaccg tcatcaccga   5520
aacgcgccag acgaaagggc ctcgtgatac gcctattttt ataggttaat gtcatgataa   5580
taatggtttc ttagacgtca ggtggcactt ttcggggaaa tgtgcgcgga acccctattt   5640
gtttattttt ctaaatacat tcaaatatgt atccgctcat gagacaataa ccctgataaa   5700
tgcttcaata atattgaaaa aggaagagta tgagtattca acatttccgt gtcgccctta   5760
ttcccttttt tgcggcattt tgccttcctg tttttgctca cccagaaacg ctggtgaaag   5820
taaaagatgc tgaagatcag ttgggtgcac gagtgggtta catcgaactg gatctcaaca   5880
gcggtaagat ccttgagagt tttcgccccg aagaacgttt tccaatgatg agcactttta   5940
aagttctgct atgtggcgcg gtattatccc gtattgacgc cgggcaagag caactcggtc   6000
gccgcataca ctattctcag aatgacttgg ttgagtactc accagtcaca gaaaagcatc   6060
```

-continued

```
ttacggatgg catgacagta agagaattat gcagtgctgc cataaccatg agtgataaca   6120

ctgcggccaa cttacttctg acaacgatcg gaggaccgaa ggagctaacc gcttttttgc   6180

acaacatggg ggatcatgta actcgccttg atcgttggga accggagctg aatgaagcca   6240

taccaaacga cgagcgtgac accacgatgc ctgtagcaat ggcaacaacg ttgcgcaaac   6300

tattaactgg cgaactactt actctagctt cccggcaaca attaatagac tggatggagg   6360

cggataaagt tgcaggacca cttctgcgct cggcccttcc ggctggctgg tttattgctg   6420

ataaatctgg agccggtgag cgtgggtctc gcggtatcat tgcagcactg gggccagatg   6480

gtaagccctc ccgtatcgta gttatctaca cgacggggag tcaggcaact atggatgaac   6540

gaaatagaca gatcgctgag ataggtgcct cactgattaa gcattggtaa ctgtcagacc   6600

aagtttactc atatatactt tagattgatt taaaacttca tttttaattt aaaaggatct   6660

aggtgaagat cctttttgat aatctcatga ccaaaatccc ttaacgtgag ttttcgttcc   6720

actgagcgtc agaccccgta gaaaagatca aaggatcttc ttgagatcct ttttttctgc   6780

gcgtaatctg ctgcttgcaa acaaaaaaac caccgctacc agcggtggtt tgtttgccgg   6840

atcaagagct accaactctt tttccgaagg taactggctt cagcagagcg cagataccaa   6900

atactgtcct tctagtgtag ccgtagttag gccaccactt caagaactct gtagcaccgc   6960

ctacatacct cgctctgcta atcctgttac cagtggctgc tgccagtggc gataagtcgt   7020

gtcttaccgg gttggactca agacgatagt taccggataa ggcgcagcgg tcgggctgaa   7080

cggggggttc gtgcacacag cccagcttgg agcgaacgac ctacaccgaa ctgagatacc   7140

tacagcgtga gctatgagaa agcgccacgc ttcccgaagg gagaaaggcg gacaggtatc   7200

cggtaagcgg cagggtcgga acaggagagc gcacgaggga gcttccaggg ggaaacgcct   7260

ggtatcttta tagtcctgtc gggtttcgcc acctctgact tgagcgtcga tttttgtgat   7320

gctcgtcagg ggggcggagc ctatggaaaa acgccagcaa cgcggccttt ttacggttcc   7380

tggccttttg ctggcctttt gctcacatgt tctttcctgc gttatcccct gattctgtgg   7440

ataaccgtat taccgccttt gagtgagctg ataccgctcg ccgcagccga acgaccgagc   7500

gcagcgagtc agtgagcgag gaagc                                         7525
```

<210> SEQ ID NO 10
<211> LENGTH: 10034
<212> TYPE: DNA
<213> ORGANISM: Artificial
<220> FEATURE:
<223> OTHER INFORMATION: Plasmid

<400> SEQUENCE: 10

```
aattctaata cgactcacta tagagtagtg taccccctaat tacaatcact atggagacat     60

acaagattaa catttttaga gataggatca accagtgtcg aagtgctgaa gaagccaaag    120

acattgttgc tgatcttctc atggctagac atgactactt tggtagagag gtatgttatt    180

acctggatat cgaattccgg caggatgttc cagcttacga catacttctt gaatttctgc    240

cagctggcac tgctttcaac attcgcaatt gtacaccaga caattttatc attcacaatg    300

gcaagcttta tatcattgac tataaagtat caactgatca tgcatatggt caaaaaactt    360

atgaaaagta cacccagatc tttggtgatg cattgtcaga attgccgttt gattttgaag    420

ttgtgatcat ccgtgctgac cctctgcgag atactatcca tgttaattca aatcaattct    480

tggaaatatt tgggccgctc aacataaacc ttgattttac ttggttcttt aatttgcgat    540

ccctgatata tgagaaatat aaggatgacg acagattcct agaaattgtg aatcaaggtg    600
```

-continued

```
aatttacgat gactggaccc tggattgatg aggatacccc ggagctctat tcacaccctg    660
tctttttgga attctatgat tctttagatg agatggctaa actgacattc catgagtcta    720
tgacatttga tgcaactcgc ggtgagaaat ggaatcaaaa tctacaaaag gttataaata    780
gatatggcaa tgattataac atttttgtga aagaggccgc tgcaggaatc tttagatgtg    840
aagggaacta cccaaaacca aatcatgatg aaatcacaat cggttggaat caaatggttc    900
aaagagtgag tactgagaga aacctgactc aagatgtcag caagcaaaaa ccatctattc    960
atttcatatg ggtcaacct gacgaaacat caaatgcgac aacaccaaaa ctaatcaaga   1020
ttgcaaaagc actccaaaat atttctggcg agtctacata tataagcgca ttcagagcat   1080
tgggtatgct tatggacttt tctgagaaca cagctttata tgaagcacac actagcaaac   1140
taaaaagtat ggcaagacag acatcgaaaa gaattgatac taaactggaa ccaatcaaaa   1200
taggcacggc gacaatttat tgggaacagc agtttaaact ggatactgaa ataatgaata   1260
caaaagacaa atcacatttg ctaaaagatt ttcttggcat agggggtcac gtgcaatttt   1320
caaaaaagac cattgacgat ttggatactg acaaacctac tatattagat ttcaacaaaa   1380
aggaagtcat tgatttttgc aaattccagt atgaaaatgt aaagaaaata ctatccggag   1440
ataataatct agagcgtata ggatgttatt tagaagaata tggtgcaaat attgcatcat   1500
gttcaaagga tacatgggat cagattaacc agatagggaa gtcaaattac tgggcttgta   1560
ttaaagattt ttcagtcttg atgaaaaata tgttggcagt ttctcaatat aataggcaca   1620
atacttttcg tgtagtgtgt tgtgcaaaca ataatctgtt tgggtttgta atgccttctt   1680
ctgatattaa agcaaagcga tccacacttg tttacttctt agctgtgttg cattctactc   1740
ctcagaatgt gatgcaccac ggtgcattgc atgcgacatt taaaactggt tcaaaatacc   1800
ttagtatctc taaaggaatg cgtttagata aagaacgatg tcaacgcata gttagttcac   1860
cgggactttt tatgttgact acattgatgt ttgcaggaga caatccgaca ctcaatttga   1920
ctgatgtcat gaattttaca ttccacactt ccctgtctat aaccaaagct atgctgtcat   1980
tgacagaacc atcaagatat atgataatga attcattagc catatccagt catgttagag   2040
attatatagc agaaaaattt ggcccttata caaagaccag cttctctgta gtaatggcaa   2100
acttgattaa aaggggatgt tatatggcat ataatcaaag agataaagta gacatgagga   2160
atatctgcct aacagattat gaaataactc aaaaaggtgt gagagataac agagacctat   2220
catcaatctg gtttgaaggc tatgtatcac taaaagaata tattaaccaa atatatctac   2280
cattttactt caattcaaaa ggtttgcatg aaaagcatca tgttatgata gatctggcta   2340
agacaatctt agatatagaa agggaccaga gattaaatat cccaggaata tggtctacaa   2400
cacctagaaa acaaactgca aatttaaata taactatcta tgcagttgca aaaaatctaa   2460
taatggacac tgctagacat aattatatta gatcacggat agaaaacaca aacaacttaa   2520
atagatcgat atgcactatt tctacattca ccagctctaa atcatgtatt aaagtaggcg   2580
actttgagaa agaaaaaagc tcagcaacaa aaaaggctgc agattgcatg tcaaaagaga   2640
taaagaagta tacaattgca aacccagaat ttgttgatga agagttacta aatgcaacta   2700
taagacattc acgctatgaa gacttaaaaa aagcaatccc gaattatatt gacattatgt   2760
caactaaagt atttgattct ctgtaccaga aaataaaaag gaaggagata gatgataaac   2820
ccactgtgta tcatatactc tctgctatga agaatcacac agattttaag tttacattct   2880
ttaacaaagg ccaaaaaaca gcaaaggata gggaaatatt cgtaggcgaa tttgaggcaa   2940
aaatgtgctt gtatttagtg gagaggatat ctaaagaacg ctgtaagttg aatccagatg   3000
```

-continued

```
agatgattag tgaaccaggc gattctaaat tgaaaaaatt agaagagctt gcagagtctg   3060
aaatacgatt cacagcagca actatgaaac agatcaaaga acgctattta gcagaaatgg   3120
gagaagcaag ccatatgatc gcatataaac cacattctgt taagattgaa atcaatgcag   3180
acatgtcaaa atggagtgcc caagatgttt tattcaaata tttctggttg tttgcattag   3240
atcccgcact ttatctgcaa gaaaaagaaa ggatattgta cttcctatgc aattatatgc   3300
aaaaaaagct aattctgcct gatgaaatgc tctgtagcat ccttgaccaa cgtatcaaac   3360
atgaggatga tataatatat gaaatgacca atggcttatc gcaaaattgg gtcaatatta   3420
aacggaactg gctgcagggg aatctcaatt acacaagtag ctacctacat tcatgttcta   3480
tgaatgttta taaggatatt ctaaagagag cagccacttt actagaaggg gaagttttag   3540
tcaattctat ggttcattct gatgacaatc acacttcaat agtgatgatc caagataaat   3600
tagatgatga tattgttatt gaattttctg caaaactatt tgaaaaaata tgtctaactt   3660
ttggaaatca agcaaatatg aagaagacat atataacaaa tttcataaag gagttcgttt   3720
cactttttaa tatttatggt gagccatttt ctgtttatgg tcgctttatt ttgacatctg   3780
ttggcgattg tgcttttctt ggaccatatg aggatgttgc cagtaggttg tctgcaacgc   3840
agacagcaat taagcatgga gcacctccat cacttgcatg gactgctatt gcattaactc   3900
agtggataac acatagcaca tataacatgc ttccaggtca aatcaatgat cctacttcat   3960
ctttacctag tcatgataga tttgagctgc ctatagaatt gtgtggctta ataaattcag   4020
aattacccac tatagctata gcaggtttgg aagcagataa tctaagttat ttagttaggt   4080
tatcaaaaag aatgtcccct atacatcttt gccgtgaacc aatccagcat caatatgaga   4140
atatacatac atgggatata agtaaactga cacaatgtga tattttcaga cttaagcttt   4200
taagatacat gacgttagac tcaactatgt catctgatga tggaatgggc gaaactagtg   4260
aaatgagatc taggtctctt ctgacaccaa gaaaattcac tactgcaagt tcgttatcta   4320
gattgcattc atatgctgat tatcaaaaaa caatacaaga ccaacagaaa attgaagaat   4380
tatttgaata ttttatagcc aaccctcaac tattggttac aaaaggtgag acttgtgaag   4440
agttctgtat gtctgtattg ttcagataca acagtcgtaa atttaaagaa tcattgtcta   4500
ttcaaaaccc agctcagctc ttcatagaac aagtattgtt tgcaaataaa ccaatgatag   4560
actatacaag tattcatgat aggttgtttg gtatacaaga tgacccaaat ataaatgatg   4620
ctacatgtat tattggcaag aagacttttg ttgaaacata tcagcaaata aaaattgatg   4680
tagaaaaatt tacacttgat gtagaggata taaagacgat atatagcttc tgtataatga   4740
acgaccctat attagttgct tgtgcaaaca acttgttaat ttcaatacag ggagtggaga   4800
tgcaacgatt gggtatgaca tgctgttata tgccggagat taagagcctt aaagtaattt   4860
atcatagtcc tgctctcgta ttacgtgctt atgtaacaga taactatgag caaaaaggga   4920
tggagccaga tgaaatgcgg agagatatat atcatttaga agaatttata gagaagacaa   4980
aattgaggac aaatatgcaa gggagaattg caaataatga aattaagtta atgaagcgag   5040
atttgaaatt tgaagtgcag gaattgacta aattctatca gatctgttat gaatatgtga   5100
aatcaacaga acacaaaatt aaaatattca tccttccaaa aaaggcttac actcccattg   5160
atttctgctc attagtaaca ggtaatctga tatcagacaa caaatggatg gttgttcact   5220
atttaaaaca aataactgtc ccagcaaaga aggcacaaat agccacatct atagatctgg   5280
aaatacaaat agcctacgaa tgtttcaggc taattgcaca ttttgctgat atgttcctaa   5340
atgatgactc caaaaaagct tatattaatg caattattaa cacatataca tacaaggatg   5400
```

-continued

```
ttcaagtatc cagtctctac aagaaaatca aaaattcgag actacgttca aaaattatac   5460
cattattata tcacctgggc gatttgcaac aaatagacgt tgacagattt gatgcagaaa   5520
aagcagaaga gcagatcaca tggaataact ggcaaacatc tcgagaattt actactggtc   5580
caattgatct atcaatcaaa ggttatggac ggtcaataag gatcgtaggt gaggacaaca   5640
agcttacagc tgcagaaatg caattgtcaa gagtgagaag tgatatagta tcaaggcatg   5700
gacaggcttt attgaacaaa cctcatgggc taaaattaga gaaaatggaa ccagtgactg   5760
atctaaatcc taaattatgg tatattgcat accaattgcg tgagaaaaag cggtatcact   5820
atggggtctt tagtacatct tatatagaag agcataactc aaggatagaa gcatctcgga   5880
tacgtaagac taataaatgg ataccagttt gccctattgc tatatcaaaa caatcatctg   5940
atggaaagcc tagtcttgca aaaatcccta tgttaaatat tggggagatt aaatttacaa   6000
aactacagat tgcagtagat gatcatgcaa tgattaggaa agccccattt agtaagatgg   6060
tgttctttga tggcccaccc atacagagcg gtggcattga cattggaaag cttatgaaga   6120
accaaaatat tctcaatttg aggttagata atatacagag tataacatta ttagatttgt   6180
gccgcatatt ttcatgccga gggtctaaag tggatcaaga tgcatttgaa ttcttatctg   6240
atgaaccttt ggatgaagat gttattgatg aattagatag ctcacctgca ttagtggtat   6300
cttacacaaa gaaatcaacc aaatccaata gtttcaaaaa tgttatagtt agagcattga   6360
taagagaatg tgatatattt gaagatataa tggacataac agacgatgga ttcacatctg   6420
atagcaatct agaggtgtta gaaaacttaa catggatttt aaatatgctc gcaacaaatc   6480
agtggtctac agaactgtta gcatgcatac acatgtgttt atatcgcaat gagatggatc   6540
atatctatca caattttcaa gttccagaaa tatttgtcga caatccaatc tcattaaatg   6600
taaagtggga tgaagtaatt atgttcttaa acatactgcg agacagagat tacaaatttg   6660
agccatgggt gtctatactg aatcattcct taactaaagc tatagagtat gcttacaaaa   6720
agatggaaga ggagaggaag cagaaatcaa caggcatcaa caaattctta aagggtaaaa   6780
aaatgggtgg cagatcaaag tttgatttcc agtagcttga tcttaaataa tacataatct   6840
ttgccccaaa tctgtattat ataaataatt ctaaagtagt ttcatgtaat taggggcaca   6900
ctactgggtc ggcatggcat ctccacctcc tcgcggtccg acctgggcat ccgaaggagg   6960
acgcacgtcc actcggatgg ctaagggagg gatccggctg ctaacaaagc ccgaaaggaa   7020
gctgagttgg ctgctgccac cgctgagcaa taactagcat aaccccttgg ggcctctaaa   7080
cgggtcttga ggggtttttt gctgaaagga ggaactatat ccggatgggg atcctctaga   7140
gtcgacctgc aggcatgcaa gcttggcact ggccgtcgtt ttacaacgtc gtgactggga   7200
aaaccctggc gttacccaac ttaatcgcct tgcagcacat ccccctttcg ccagctggcg   7260
taatagcgaa gaggcccgca ccgatcgccc ttcccaacag ttgcgcagcc tgaatggcga   7320
atggcgcctg atgcggtatt ttctccttac gcatctgtgc ggtatttcac accgcatacg   7380
tcaaagcaac catagtacgc gccctgtagc ggcgcattaa gcgcggcggg tgtggtggtt   7440
acgcgcagcg tgaccgctac acttgccagc gccctagcgc ccgctccttt cgctttcttc   7500
ccttcctttc tcgccacgtt cgccggcttt ccccgtcaag ctctaaatcg ggggctccct   7560
ttagggttcc gatttagtgc tttacggcac ctcgacccca aaaaacttga tttgggtgat   7620
ggttcacgta gtgggccatc gccctgatag acggtttttc gccctttgac gttggagtcc   7680
acgttcttta atagtggact cttgttccaa actggaacaa cactcaaccc tatctcgggc   7740
tattcttttg atttataagg gattttgccg atttcggcct attggttaaa aaatgagctg   7800
```

-continued

```
atttaacaaa aatttaacgc gaattttaac aaaatattaa cgtttacaat tttatggtgc   7860
actctcagta caatctgctc tgatgccgca tagttaagcc agccccgaca cccgccaaca   7920
cccgctgacg cgccctgacg ggcttgtctg ctcccggcat ccgcttacag acaagctgtg   7980
accgtgtccg ggagctgcat gtgtcagagg ttttcaccgt catcaccgaa acgcgccaga   8040
cgaaagggcc tcgtgatacg cctattttta taggttaatg tcatgataat aatggtttct   8100
tagacgtcag gtggcacttt tcggggaaat gtgcgcggaa cccctatttg tttatttttc   8160
taaatacatt caaatatgta tccgctcatg agacaataac cctgataaat gcttcaataa   8220
tattgaaaaa ggaagagtat gagtattcaa catttccgtg tcgcccttat tccctttttt   8280
gcggcatttt gccttcctgt ttttgctcac ccagaaacgc tggtgaaagt aaaagatgct   8340
gaagatcagt tgggtgcacg agtgggttac atcgaactgg atctcaacag cggtaagatc   8400
cttgagagtt ttcgccccga agaacgtttt ccaatgatga gcacttttaa agttctgcta   8460
tgtggcgcgg tattatcccg tattgacgcc gggcaagagc aactcggtcg ccgcatacac   8520
tattctcaga atgacttggt tgagtactca ccagtcacag aaaagcatct tacggatggc   8580
atgacagtaa gagaattatg cagtgctgcc ataaccatga gtgataacac tgcggccaac   8640
ttacttctga caacgatcgg aggaccgaag gagctaaccg cttttttgca caacatgggg   8700
gatcatgtaa ctcgccttga tcgttgggaa ccggagctga atgaagccat accaaacgac   8760
gagcgtgaca ccacgatgcc tgtagcaatg gcaacaacgt tgcgcaaact attaactggc   8820
gaactactta ctctagcttc ccggcaacaa ttaatagact ggatggaggc ggataaagtt   8880
gcaggaccac ttctgcgctc ggcccttccg gctggctggt ttattgctga taaatctgga   8940
gccggtgagc gtgggtctcg cggtatcatt gcagcactgg ggccagatgg taagccctcc   9000
cgtatcgtag ttatctacac gacggggagt caggcaacta tggatgaacg aaatagacag   9060
atcgctgaga taggtgcctc actgattaag cattggtaac tgtcagacca agtttactca   9120
tatatacttt agattgattt aaaacttcat ttttaattta aaaggatcta ggtgaagatc   9180
ctttttgata atctcatgac caaaatccct taacgtgagt tttcgttcca ctgagcgtca   9240
gaccccgtag aaaagatcaa aggatcttct tgagatcctt tttttctgcg cgtaatctgc   9300
tgcttgcaaa caaaaaaacc accgctacca gcggtggttt gtttgccgga tcaagagcta   9360
ccaactcttt ttccgaaggt aactggcttc agcagagcgc agataccaaa tactgtcctt   9420
ctagtgtagc cgtagttagg ccaccacttc aagaactctg tagcaccgcc tacatacctc   9480
gctctgctaa tcctgttacc agtggctgct gccagtggcg ataagtcgtg tcttaccggg   9540
ttggactcaa gacgatagtt accggataag gcgcagcggt cgggctgaac ggggggttcg   9600
tgcacacagc ccagcttgga gcgaacgacc tacaccgaac tgagatacct acagcgtgag   9660
ctatgagaaa gcgccacgct tcccgaaggg agaaaggcgg acaggtatcc ggtaagcggc   9720
agggtcggaa caggagagcg cacgagggag cttccagggg gaaacgcctg gtatctttat   9780
agtcctgtcg ggtttcgcca cctctgactt gagcgtcgat ttttgtgatg ctcgtcaggg   9840
gggcggagcc tatggaaaaa cgccagcaac gcggcctttt tacggttcct ggccttttgc   9900
tggccttttg ctcacatgtt ctttcctgcg ttatcccctg attctgtgga taaccgtatt   9960
accgcctttg agtgagctga taccgctcgc cgcagccgaa cgaccgagcg cagcgagtca  10020
gtgagcgagg aagc                                                    10034
```

INFECTIOUS SCHMALLENBERG VIRUS FROM CLONED CDNAS AND USES THEREOF

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

1. Technical Field

The present invention belongs to the field of animal health and relates to nucleic acid sequences comprising the complete genome sequences of the genome segments of an infectious Schmallenberg virus. The invention also relates to the use of the nucleic acid sequences for producing infectious Schmallenberg virus to study the viremia and clinical symptoms induced by Schmallenberg virus in ruminants, and in the development of vaccines, therapeutics and diagnostics for the prophylaxis, treatment and diagnosis of a Schmallenberg virus infection.

2. Background Information

A novel orthobunyavirus, the Schmallenberg virus (SBV), was discovered in Europe in November 2011. After the first detection, the reported cases of SBV in sheep, cattle, and goats dramatically accumulated in several European countries to several thousand cases of PCR-positive malformed lambs and calves (1, 2). The virus was detected by metagenomics at the Friedrich-Loeffler-Institut (ELI) in samples of cattle with milk drop and fever. The investigated samples were collected in a farm near the city of Schmallenberg (North Rhine-Westphalia, Germany), and consequently the virus was named Schmallenberg virus (SBV). SBV is a member of the genus Orthobunyavirus within the family Bunyaviridae. It is related to the so-called Simbu serogroup viruses (1). SBV is like Akabane virus (AKAV) able to cross the placental barrier in pregnant cows and sheep, infect the fetus and cause fatal congenital defects during a susceptible stage in pregnancy (2). Therefore, SBV is a serious threat to ruminant livestock in Europe since vaccines are currently not available.

Orthobunyaviruses have a segmented, negative stranded RNA genome and are mainly transmitted by insect vectors like midges and mosquitis. The three segments (S, M and L) of the Orthobunyavirus genome allow genetic reassortment, which naturally occurs resulting in the emergence of viruses with new biological properties (3). The largest segment L encodes the RNA-dependent RNA polymerase. The M-segments encodes the viral surface glycoproteins Gn and Gc which are responsible for cell fusion, viral attachment and the induction of neutralizing antibodies. The small S-segment encodes the nucleocapsid N which is also involved in complement fixation (4). The relationship between Orthobunyaviruses were often only determined by serological cross-reactivity (5). In the era of DNA sequencing, phylogenetics has additionally been assessed by comparison of partial genome sequences (full N and partial Gc gene) (6). Therefore, available and published genome sequence information of full-length genomes is sparse. As a consequence, in-depth phylogenetic analyses are difficult. In conclusion, a detailed and reliable taxonomic classification of SBV could not be made. Preliminary investigations showed similarities of the M- and L-segment sequences to partial AKAV and Aino virus (AINOV) sequences. The N gene was most closely related to Shamonda virus (SHAV) (1).

SBV was the first orthobunyavirus of the Simbu serogroup detected in Europe. The virus is apparently transmitted by arthropod vectors. Biting midges probably play an important role in transmission. According to the current state of knowledge, ruminants are susceptible to infection with SBV. Adult animals may develop mild disease, if any. However, transplacental infection occurs frequently and can lead to severe congenital malformation of the vertebral column (Kyphosis, lordosis, scoliosis, torticollis) and of the scull (macrocephaly, brachygnathia inferior) as well as variable malformations of the brain (hydrancenphaly, porencephaly, cerebellar hypoplasia, hypoplasia of the brain stem) and of the spinal cord in lambs, kids and calves. The infection spread rapidly over large parts of North Western Europe. Belgium, Germany, France, Italy, Luxembourg, the Netherlands, Spain and the United Kingdom have been affected so far.

The Simbu serogroup, named according to the prototype virus, is the largest serogroup of Orthobunyavirus and contains at least 25 viruses, among them medically important viruses such as Akabane virus, Oropouche virus, Sathuperi virus or Douglas virus, most of which can cause malformations in new born ruminants, but also human beings can be affected. Akabane virus, for instance, causes congenital defects in ruminants and circulates in Asia, Oceania and Africa, whereas Oropouche virus is responsible for large epidemics of Oropouche fever, a zoonosis similar to dengue fever, in human populations in South Africa. Sathuperi virus has lent his name to the Sathuperi serogroup, to which belong also Douglas virus and SBV.

Reverse genetic systems for Bunya viruses are technically challenging, which is reflected by a small number of publicated systems. For Orthobunyaviruses a minigenome system (7), a transcription and replication competent trVLP (virus like particle) system (8) and full-length clone systems (9, 10) have been described. However, although the rescue system to recover infectious Bunyamvera virus of the Group C serogroup (genus Orthobunyavirus) entirely from cloned cDNA, that uses T7 RNA Polymerase has already been described in 1996 (9, 10), and comparable system exists for a Simbu serogroupe virus. One rescue system, which is based on cloned cDNAs but utilizes RNA polymerase I for the production of viral transcripts, had been described for Akabane virus, so far. However, there is a strong need for reverse genetic systems, particularly with regard to T7 RNA polymerase-driven systems allowing to produce infectious Schmallenberg viruses, for a better understanding of the diseases induced by said virus, for reproducing said disease in its different forms, for comparative tests, and as platform for the development of new vaccines, medications and diagnostics for the prophylaxis, treatment and diagnosis of viremia and diseases caused by SBV.

DESCRIPTION OF THE INVENTION

The solution to the above technical problem is achieved by the description and the embodiments characterized in the claims.

Thus, the invention in its different aspects is implemented according to the claims.

In one aspect, the invention provides a nucleic acid molecule, in particular a cDNA molecule, comprising the genomic sequence of a Schmallenberg virus (SBV) genome segment, in particular comprising the complete genomic sequence of a genome segment of an infectious Schmallenberg virus (SBV), wherein said molecule comprises a nucleic acid sequence selected from the group consisting of:

a nucleic acid sequence having at least 97.8% sequence identity with the nucleic acid sequence of SEQ ID NO:1 or SEQ ID NO:7, a nucleic acid sequence having at least 82.2% sequence identity with the nucleic acid sequence of SEQ ID NO:2, and a nucleic acid sequence having at least 93% sequence identity with the nucleic acid sequence of SEQ ID NO:3.

Preferably, the nucleic acid molecule of the invention comprises the genomic sequence of the S segment of Schmallenberg virus, wherein said molecule comprises a nucleic acid sequence having at least 97.8%, preferably at least 98%, more preferably at least 99%, still more preferably at least 99.5%, and in particular preferably 100% sequence identity with the nucleic acid sequence of SEQ ID NO:1 or SEQ ID NO:7, and wherein this nucleic acid molecule is also termed “nucleic acid molecule (S)” or “DNA molecule (S)” hereinafter.

In another aspect, the nucleic acid molecule of the invention comprises the genomic sequence of the M segment of Schmallenberg virus, wherein said molecule comprises a nucleic acid sequence having at least 82.2%, in particular at least 85%, more particular at least 90% or at least 95%, preferably at least 98%, more preferably at least 99%, still more preferably at least 99.5%, and in particular preferably 100% sequence identity with the nucleic acid sequence of SEQ ID NO:2, and wherein this nucleic acid molecule is also termed “nucleic acid molecule (M)” or “DNA molecule (M)” hereinafter.

In a further aspect, the nucleic acid molecule of the invention comprises the genomic sequence of the L segment of Schmallenberg virus, wherein said molecule comprises a nucleic acid sequence having at least 93%, in particular at least 95%, more particular at least 97%, preferably at least 98%, more preferably at least 99%, still more preferably at least 99.5% or at least 99.8%, and in particular preferably 100% sequence identity with the nucleic acid sequence of SEQ ID NO:3, and wherein this nucleic acid molecule is also termed “nucleic acid molecule (L)” or “DNA molecule (L)” hereinafter.

Sequence identity in the context of the invention is understood as being based on pairwise sequence alignments. For purposes of the present invention, pairwise sequence alignments are done with ClustalW as implemented in Mega5 (K. Tamura et. al., MEGA5: Molecular Evolutionary Genetics Analysis using Maximum Likelihood, Evolutionary Distance, and Maximum Parsimony Methods. Mol. Biol. Evol. 28, 2731-2739 (2011)), using the default settings (gap opening penalty of 15 and gap extension penalty of 6.66; DNA weight matrix: ClustalW 1.6; Transition weight of 0.5). Sequence identities of the aligned sequences are preferably calculated using BioEdit version 7.0.9.0.

The term “having 100% sequence identity”, as used herein, is understood to be equivalent to the term “being identical”.

As used herein, it is in particular understood that the term “sequence identity with the nucleic acid sequence of SEQ ID NO:X” is equivalent to the term “sequence identity with the nucleic acid sequence of SEQ ID NO:X over the length of SEQ ID NO: X” or to the term “sequence identity with the nucleic acid sequence of SEQ ID NO:X over the whole length of SEQ ID NO: X”, respectively. In this context, “X” is any integer selected from 1 to 10 so that “SEQ ID NO: X” represents any of the SEQ ID NOs mentioned herein.

In another aspect, the invention comprises a combination of at least two, preferably two, nucleic acid molecules selected from the group consisting of:

the nucleic acid molecule (S), i.e., as defined herein, a nucleic acid molecule comprising the genomic sequence of the S segment of Schmallenberg virus, wherein said molecule comprises a nucleic acid sequence having at least 97.8%, preferably at least 98%, more preferably at least 99%, still more preferably at least 99.5%, and in particular preferably 100% sequence identity with the nucleic acid sequence of SEQ ID NO:1 or SEQ ID NO:7, the nucleic acid molecule (M), i.e., as defined herein, a nucleic acid molecule comprising the genomic sequence of the M segment of Schmallenberg virus, wherein said molecule comprises a nucleic acid sequence having at least 82.2%, in particular at least 85%, more particular at least 90% or at least 95%, preferably at least 98%, more preferably at least 99%, still more preferably at least 99.5%, and in particular preferably 100% sequence identity with the nucleic acid sequence of SEQ ID NO:2, and the nucleic acid molecule (L), i.e., as defined herein, a nucleic acid molecule comprising the genomic sequence of the L segment of Schmallenberg virus, wherein said molecule comprises a nucleic acid sequence having at least 93%, in particular at least 95%, more particular at least 97%, preferably at least 98%, more preferably at least 99%, still more preferably at least 99.5% or at least 99.8%, and in particular preferably 100% sequence identity with the nucleic acid sequence of SEQ ID NO:3, and wherein in particular the combination of the nucleic acid molecule (S) and the nucleic acid molecule (M), preferably each having at least 98% or at least 99% sequence identity with SEQ ID NO:1 and SEQ ID NO:2, respectively, is preferred, or wherein in particular the combination of the nucleic acid molecule (S) and the nucleic acid molecule (M), preferably each having at least 98% or at least 99% sequence identity with SEQ ID NO:7 and SEQ ID NO:2, respectively, is preferred.

Preferably, the nucleic acid molecules described herein are isolated nucleic acid molecules. According to the invention, the combination of the nucleic acid molecule (S), the nucleic acid molecule (M), and the nucleic acid molecule (L) is most preferred, in particular a combination of the nucleic acid molecule (S), the nucleic acid molecule (M) and the nucleic acid molecule (L), each having at least 98% or at least 99% sequence identity with SEQ ID NO:1, SEQ ID NO:2, and SEQ ID NO:3, respectively, or in particular a combination of the nucleic acid molecule (S), the nucleic acid molecule (M) and the nucleic acid molecule (L), each having at least 98% or at least 99% sequence identity with SEQ ID NO:7, SEQ ID NO:2, and SEQ ID NO:3, respectively.

The term “combination”, as used herein, in particular refers to any bringing together or admixture of the nucleic acid molecules, of the DNA constructs, preferably the cDNA constructs or of the RNA transcripts to be combined according to the invention, or preferably refers to a composition containing the nucleic acid molecules, the DNA constructs, preferably the cDNA constructs or the RNA transcripts of the combination.

Preferably, the combination of the nucleic acid molecule (S), the nucleic acid molecule (M), and the nucleic acid molecule (L), is capable of producing infectious Schmallenberg virus when transfected into cells. Since Schmallenberg virus has a negative stranded RNA genome, the presence of an RNA polymerase, preferably of T7 RNA polymerase or the RNA polymerase encoded by the Schmallenberg virus, in the transfected cells is required. Most preferred is the use of the T7 RNA polymerase. The presence of the RNA polymerase in the transfected cells can be provided, for instance, by co-transfection of a plasmid coding for and expressing the RNA polymerase or by penetrating the cells with RNA polymerase protein. According to the invention, in this regard, the use of transgenic cells producing RNA polymerase is particularly preferred, such as the transfection of the combination of the nucleic acid molecule (S), the nucleic acid molecule (M), and the nucleic acid molecule (L) into BSR-T7/5 cells. Alternatively, the cells can also be transfected with the mRNA that codes for the RNA polymerase and which is translated into the RNA polymerase when transfected into the host cells.

In two exemplary embodiments, the transfection may be performed with or without the co-transfection of at least one, preferably two or three, helper plasmid(s).

The term "infectious Schmallenberg virus" according to the invention is in particular understood as a Schmallenberg virus which infects mammals and/or insects and causes viremia in the infected mammal and/or insect.

As used herein, the term "viremia" is particularly understood as a condition in which Schmallenberg virus particles reproduce and circulate in the bloodstream of an animal, in particular of a mammal or of an insect.

Said infection of a mammal and/or insect by the Schmallenberg virus being produced by the nucleic acid molecules of the present invention in particular includes attachment of the virus to a host cell, entry of the virus into the cell, uncoating of the virion in the cytoplasm, replication and transcription of the viral genome, expression of viral proteins and assembly and release of new infectious viral particles.

Preferably, the mammal as mentioned herein is a ruminant, in particular selected from the group consisting of cattle, sheep, goats, deer, elk, giraffes, bison, moose, yaks, water buffalo, camels, alpacas, llamas, antelope, pronghorn, and nilgai. More preferably, the mammal as mentioned herein is a ruminant selected from the group consisting of cattle, sheep and goats.

The insect, as mentioned herein, is preferably selected from the group consisting of midges, in particular *Culicoides* spp., biting flies and mosquitoes.

The term "helper plasmids" as mentioned herein, is in particular directed to plasmids that contain one or more SBV coding sequence(s), e.g. under the control of a T7 promotor, to express the protein(s) of SBV.

The present invention further provides a DNA construct, preferably a cDNA construct, comprising the cDNA molecule according to the invention, wherein said DNA construct is in particular a cDNA vector such as a plasmid.

Herein, the DNA construct. preferably the cDNA construct, of the present invention which comprises the cDNA molecule (S) is also termed "DNA construct (S)", the DNA construct of the present invention which comprises the DNA molecule (M) is also termed "DNA construct (M)", and the DNA construct of the present invention which comprises the DNA molecule (L) is also termed "DNA construct (L)".

According to the invention, preferred DNA vectors or plasmids into which the nucleotide molecule of the present invention can be inserted are pGEM-T Easy, pUC18, pcDNA, pX8δT or pT7riboSM2. The cDNA construct, as described herein, is preferably an isolated cDNA construct.

Exemplary cDNA constructs of the invention are provided with the sequences set forth in SEQ ID NOs: 4-6, wherein SEQ ID No: 4 shows an example of the sequence of a DNA construct (S), SEQ ID No: 5 shows an example of the sequence of a DNA construct (M) and SEQ ID No: 6 shows an example of the sequence of a DNA construct (L). Further exemplary cDNA constructs of the invention are provided with the sequences set forth in SEQ ID NOs: 8-10, wherein SEQ ID No: 8 shows an example of the sequence of a DNA construct (S), SEQ ID No: 9 shows an example of the sequence of a DNA construct (M) and SEQ ID No: 10 shows an example of the sequence of a DNA construct (L).

The invention also provides a combination of at least two, preferably two, different DNA constructs selected from the group consisting of:

- the DNA construct (S), i.e., as defined herein, a cDNA construct which comprises the DNA molecule (S),
- the DNA construct (M), i.e., as defined herein, a cDNA construct which comprises the DNA molecule (M), and

- the DNA construct (L), i.e., as defined herein, a cDNA construct which comprises the DNA molecule (L), wherein the at least two different cDNA constructs are preferably isolated cDNA constructs, and wherein in particular the combination of the DNA construct (S) and the DNA construct (M) is preferred, preferably each comprising the nucleic acid molecule (S) or the nucleic acid molecule (M), respectively, having at least 98% or at least 99% sequence identity with SEQ ID NO:1 or SEQ ID NO:2, respectively, or preferably each comprising the nucleic acid molecule (S) or the nucleic acid molecule (M), respectively, having at least 98% or at least 99% sequence identity with SEQ ID NO:7 or SEQ ID NO:2, respectively.

According to the invention, the combination of the DNA construct (S), the nucleic acid molecule (M), and the nucleic acid molecule (L), is most preferred, in particular each comprising the nucleic acid molecule (S), the nucleic acid molecule (M) or the nucleic acid molecule (L), respectively, having at least 98% or at least 99% sequence identity with SEQ ID NO:1, SEQ ID NO:2, or SEQ ID NO:3, respectively, or in particular each comprising the nucleic acid molecule (S), the nucleic acid molecule (M) or the nucleic acid molecule (L), respectively, having at least 98% or at least 99% sequence identity with SEQ ID NO:7, SEQ ID NO:2, or SEQ ID NO:3, respectively.

Further, the invention provides a preferably isolated RNA transcript of the cDNA construct of the invention.

In the following, the RNA transcript of the DNA construct (S) of the present invention is also termed "RNA transcript (S)", the RNA transcript of the DNA construct (M) of the present invention is also termed "RNA transcript (M)", and the RNA transcript of the DNA construct (L) is also termed "RNA transcript (L)".

The invention also provides a combination of at least two, preferably two, different RNA transcripts, preferably isolated RNA transcripts, selected from the group consisting of:

- the RNA transcript (S), i.e., as defined herein, the RNA transcript of the DNA construct (S),
- the RNA transcript (M), i.e., as defined herein, the RNA transcript of the DNA construct (M), and

- the RNA transcript (L), i.e., as defined herein, the RNA transcript of the DNA construct (L), wherein in particular the combination of the RNA transcript (S) and the RNA transcript is preferred, preferably transcribed from the DNA construct (S) and the DNA construct (M), respectively, each comprising the nucleic acid molecule (S) or the nucleic acid molecule (M), respectively, having at least 98% or at least 99% sequence identity with SEQ ID NO:1 or SEQ ID NO:2, respectively, or preferably transcribed from the DNA construct (S) and the DNA construct (M), respectively, each comprising the nucleic acid molecule (S) or the nucleic acid molecule (M), respectively, having at least 98% or at least 99% sequence identity with SEQ ID NO:7 or SEQ ID NO:2, respectively.

According to the invention, the combination of the RNA transcript (S), the RNA transcript (L), and the RNA transcript (M), is most preferred, in particularly transcribed from the DNA construct (S), the DNA construct (M) and the DNA construct (L), respectively, each comprising the nucleic acid molecule (S), the nucleic acid molecule (M) or the nucleic acid molecule (L), respectively, having at least 98% or at least 99% sequence identity with SEQ ID NO:1, SEQ ID NO:2 or SEQ ID NO:3, respectively, or in particularly transcribed from the DNA construct (S), the DNA construct (M) and the DNA construct (L), respectively, each comprising the nucleic acid molecule (S), the nucleic acid molecule (M) or the nucleic acid molecule (L), respectively, having at least 98% or at least 99% sequence identity with SEQ ID NO:7, SEQ ID NO:2 or SEQ ID NO:3, respectively.

The present invention also provides a cell transfected with the DNA construct described herein or with the combination of DNA constructs described herein, wherein said cell is preferably an isolated cell.

Thus, the present invention also provides Schmallenberg virus produced by the aforementioned cell, wherein said Schmallenberg virus is preferably an isolated Schmallenberg virus. Furthermore, the present invention also provides a cell, preferably a cultured host cell which comprises the Schmallenberg virus produced by or in the presence of one or more of the nucleic acid constructs provided herein.

Further, the present invention provides a cell transfected with the RNA transcript mentioned herein or with the combination of RNA transcripts mentioned herein, wherein said cell is preferably an isolated cell.

Hence, the present invention also provides Schmallenberg virus produced by the aforementioned cell, wherein said Schmallenberg virus is preferably an isolated Schmallenberg virus.

The present invention further provides a Schmallenberg virus whose genome comprises the nucleic acid molecule of the present invention or the combination of nucleic acid molecules of the present invention, wherein said Schmallenberg virus is preferably an isolated Schmallenberg virus In another aspect, the present invention provides a method for producing a Schmallenberg virus, said method comprising transfecting a cell with the DNA construct or with the combination of DNA constructs described herein.

Moreover, the present invention provides a method for producing a Schmallenberg virus, said method comprising transfecting a cell with the RNA transcript or with the combination of RNA transcripts mentioned herein.

Since Schmallenberg virus has a negative stranded RNA genome, preferably the method of producing the Schmallenberg virus is done in the presence of an RNA polymerase, preferably of T7 RNA polymerase or the RNA polymerase encoded by the Schmallenberg virus. Most preferred is the use of the T7 RNA polymerase. The presence of the RNA polymerase in the transfected cells can be provided, for instance, by co-transfection of a plasmid coding for and expressing the RNA polymerase. According to the invention, in this regard, the use of transgenic cells producing RNA polymerase is particularly preferred, such as the transfection of the combination of the nucleic acid molecule (S), the nucleic acid molecule (M), and the nucleic acid molecule (L) into BSR-T7/5 cells. Alternatively, the cells can also be transfected with the mRNA that codes for the RNA polymerase and which is translated into the RNA polymerase when transfected into the host cells.

In yet another aspect, the present invention provides a composition, said composition comprising the nucleic acid molecule according to the invention or the combination of nucleic acids according to the invention, suspended in a suitable amount of a pharmaceutically acceptable diluent or excipient.

Production of the nucleic acid molecules described herein is within the skill in the art and can be carried out according to recombinant techniques described, among other places, in Sambrook et al., 2001, Molecular Cloning, A Laboratory Manual, Cold Spring Harbor Laboratory Press, Cold Spring Harbor, N.Y.; Ausubel, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

EXAMPLE 1

Establishment of a reverse genetics system for the generation of recombinant SBV, which allows further investigation on the molecular biology of Orthobunyaviruses as well as the generation of save and efficient vaccines.

SBV was isolated from infected cattle and passaged on KC cells and BHK-21 cells. RNA was extracted from infected cells and transcribed into cDNA. PCR fragments of the three RNA segments were amplified by using gene specific primers and were inserted into the plasmid pX8δT (11) by restrictions-free cloning (13). The resulting plasmids pX8δT_SBV_S, pX8δT_SBV_M and pX8δT_SBV_L contain the full-length antigenome of SBV.

Transfection experiments are done by using BSR T7/5 cells, stably expressing the phage T7 polymerase (12) and plasmid DNA of all of the three constructs pX8δT_SBV_S, pX8δT_SBV_M and pX8δT_SBV_L. Supernatants of the cells are harvested after various times following transfection and transferred to susceptible cell lines. The cell monolayers are investigated for expression of SBV proteins by indirect immunofluorescence staining.

Results

Three cDNA clones spanning the complete genomic sequence of the segments S, M and L were generated from viral RNA by fusion PCR. RNA transcripts were produced by bacteriophage T7 polymerase in BSR T7/5 cells. The exact 3' end of the RNA is specified by self-cleavage of the RNA by the hepatitis delta virus antigenome ribozyme sequence. Rescue of infectious SBV, growth characteristics of recombinant viruses and manipulation of the full-length genome like the deletion of relevant domains can be demonstrated.

Conclusions

A reverse genetic system for the recovery of SBV, the first European Simbu serogroup virus, can be established. The new system can be used for the generation of recombinant SBV, by transfection of cells stably expressing phage T7 RNA polymerase with the plasmids pX8δT_SBV_S, pX8δT_SBV_M pX8δT_SBV_L allowing expression of antigenomic SBV RNA and the viral proteins. By using SBV reverse genetics, defined mutants can be designed enabling the mechanistic investigation of virus-host interactions as well as the molecular basis of SBV pathogenesis. Furthermore, the approach will be useful for the design of next generation vaccines like packaged replicons and defective in second cycle virions, chimera or modified deletion mutants.

In the following, the construction of the plasmids pX8δT_SBV_S, pX8δT_SBV_M and pX8δT_SBV_L and the transfection and recovery of recombinant SBV, as mentioned above, is described in closer detail.

Figure 1B:
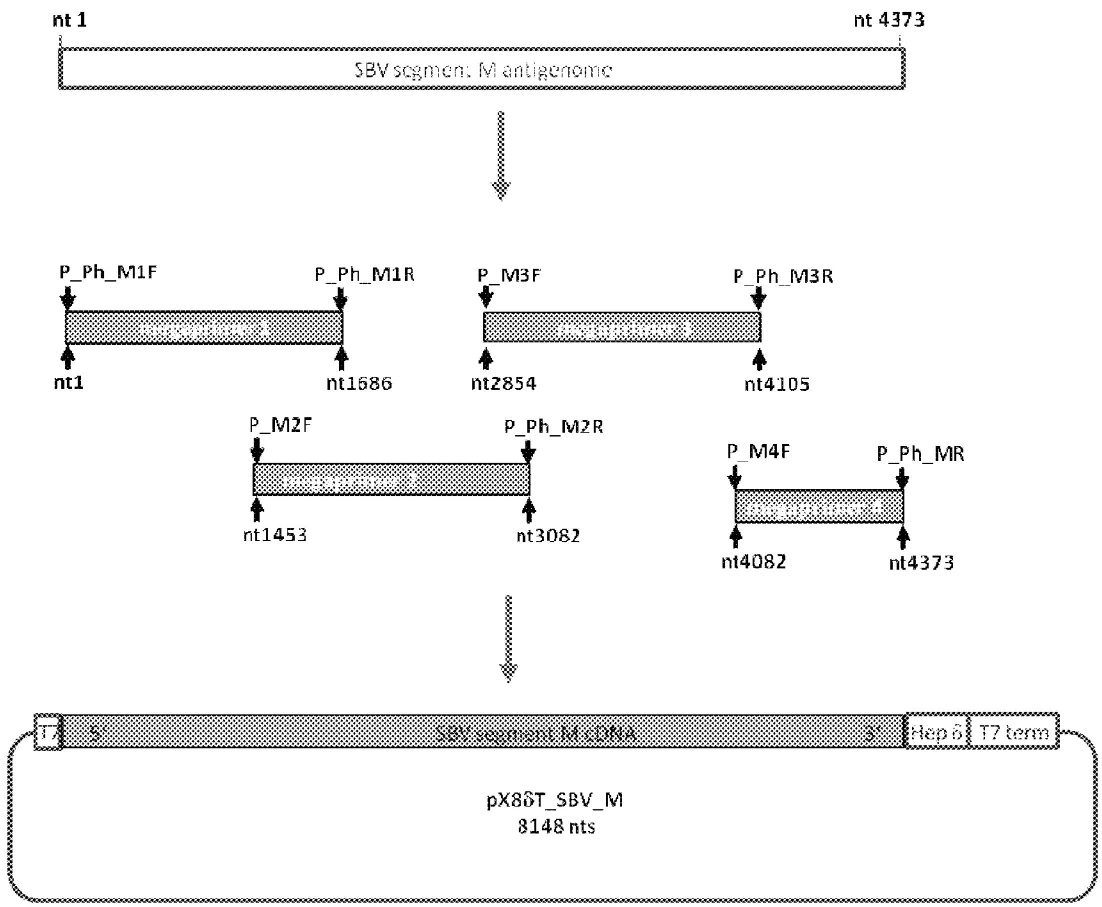
Figure 1C:
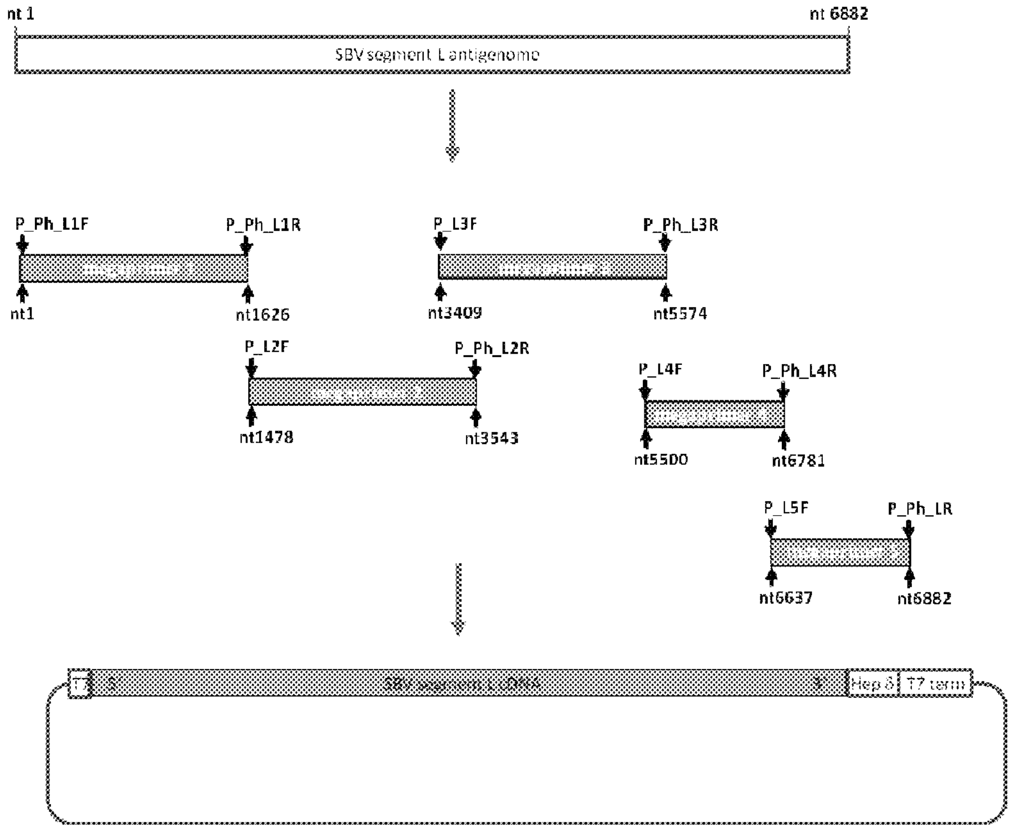

The construction of the plasmids pX8δT_SBV_S, pX8δT_SBV_M and pX8δT_SBV_L was done by using the plasmid vector X8δT (11). cDNA of the Schmallenberg Virus (SBV) RNA segments was inserted into this plasmid by restrictions-free cloning (fusion PCR) (13), respectively. The construction of the cDNA clones is shown in FIG. 1A-1C. The plasmids contain a bacteriophage T7 promotor (T7) before 5' SBV cDNA to enable in vitro transcription of cDNA into RNA, the Hepatitis delta virus ribozyme sequence (Hep δ for the generation of the exact 3' end by self-cleavage of the nascent RNA by the Hepatitis delta virus antigenome ribozyme and the T7 transcription termination sequence (T7 term) downstream the 3' end of the SBV cDNA. Location of the used primers and nucleotide positions corresponding to the Schmallenberg antigenome are indicated by arrows.

RNA of Schmallenberg virus (BH80/11-4) infected BHK 21 cells was isolated by using QIAmp viral RNA Mini Kit (Qiagen) and transcribed by using the Transcriptor High Fidelity cDNA Synthesis Kit (Roche). Plasmids were amplified in *Escherichia coli* DH10B™ cells (Invitrogen). For Megaprimer-PCR and fusion PCR the Phusion High Fidelity PCR Master Mix with HF Buffer (New England Biolabs) and Phusion High-Fidelity Master Mix (Finnzymes) were used. Plasmid DNA was purified by using Qiagen Plasmid Mini or Midi Kit (Qiagen). Sequencing was carried out using the Big Dye® Terminator v1.1 Cycle sequencing Kit (Applied Biosystems). Nucleotide sequences were read with an automatic sequencer (3130 Genetic Analyzer, Applied Biosystems) and analyzed using the Genetics Computer Group software version 11.1 (Accelrys Inc., San Diego, USA). Primers were synthesized by biomers.net GmbH and are listed in table 1.

TABLE 1

Nucleotide sequence of primers used for Megaprimer-PCR and fusion PCR

| Primer | Sequenz 5' → 3'[a] | Genomic region |
|---|---|---|
| P_Ph_S1F | CTTGTAATACGACTCACTATA*GGG*AGTAGTG AGCTCCACTATTAAC | 1-22[a] (+sense) |
| P_Ph_S1 | GTGGAGATGCCATGCCGACCCAGTAGTGTTC TCCACTTATTAAC | 830-808[a] (-sense) |
| P_Ph_M1F | CTTGTAATACGACTCACTATA*GGG*AGTAGTG AACTACCACAATC | 1-20[b] (+sense) |
| P_Ph_M1R | GTGGAGATGCCATGCCGACCCGCACTTGGAG AGGGCACAACTG | 1686-1665[b] (-sense) |
| P_M2F | CTCAGCTTACAATAGAGCACC | 1453-1473[b] (+sense) |
| P_Ph_M2R | GTGGAGATGCCATGCCGACCCGTGACCCAAC CATCTTGATG | 3080-3063[b] (-sense) |
| P_M3F | TCGAGTCGCACATCCCTGC | 2854-2872[b] (+sense) |
| P_Ph_M3R | GTGGAGATGCCATGCCGACCCGTCAGTCTCC AATaGAAAGATAGG | 4105-4082[b] (-sense) |
| P_M4F | CCTATCTTTCTATTGGAGACTGAC | 4082-4105[b] (+sense) |
| P_Ph_MR | GTGGAGATGCCATGCCGACCCAGTAGTGTTCTAC CACATG | 4373-4355[b] (-sense) |
| P_Ph_L1F | CTTGTAATACGACTCACTATA*GGG*AGTAGTG TACCCCTAATTACAATC | 1-24[c] (+sense) |
| P_Ph_L1R | GTGGAGATGCCATGCCGACCCGTTTGCACAA CACACTACACG | 1626-1606[c] (-sense) |
| P_L2F | GTTCAAAGGATACATGGGATCAG | 1478-1500[c] (+sense) |
| P_Ph_L2R | GTGGAGATGCCATGCCGACCCGTCATCAGAA TGAACCATAG | 3543-3524[c] (-sense) |
| P_L3F | CTGCAGGGGAATCTCAATTACAC | 3409-343[c] (+sense) |
| P_Ph_L3R | GTGGAGATGCCATGCCGACCCGATTGATAGA TCAATTGGACCAGTAG | 5570-55494[c] (-sense) |
| P_L4F | GCAGAAGAGCAGATCACATGG | 5500-5520[c] (+sense) |
| P_Ph_L4R | AGGTGGAGATGCCATGCCGACCCCAAACTTT GATCTGCCACCC | 6781-6762[c] (-sense) |
| P_L5F | GAGCCATGGGTGTCTATACTG | 6637-6657[c] (+sense) |
| P_Ph_LR | GTGGAGATGCCATGCCGACCCAGTAGTGTGC CCCTAATTACATG | 6882-6862[c] (-sense) |

[a]nucleotide position corresponding to SBV segment S sequence (unpublished)
[b]nucleotide position corresponding to SBV segment M sequence (unpublished)
[c]nucleotide position corresponding to SBV segment L sequence (unpublished)

Sequences derived from plasmid X8δT are underlined, and three additional G residues are in italics.

Construction of pX8δT_SBV_S (FIG. 1A): In a first step segment S cDNA was synthesized with primer P_Ph_S1F and used as template for the generation of a megaprimer PCR fragment. As primers P_Ph_S1F and P_Ph_S1R were utilized. By fusion PCR, SBV segment S sequences were introduced into the plasmid pX8δT.

Construction of pX8δT_SBV_M (FIG. 1B): In a multi-step cloning procedure the cDNA clone pX8δT_SBV_M was constituted from four megaprimer PCR fragments which were assembled into plasmid vector pX8δT by fusion PCR. In a first step segment M cDNA was synthesized with primer P_Ph_M1F and P_M3F and used as template for the generation of the megaprimers 1, 2, 3 and 4, respectively. As primers for the generation of megaprimer 1 primers P_Ph_M1F and P_Ph_M1R, for the generation of megaprimer 2 the primers P_M2F and P_Ph_M2R, for the generation of megaprimer 3 the primers P_M3F and P_Ph_M3R and for the generation of megaprimer 4 the primers P_M4F and P_Ph_MR were used. By fusion PCR the megaprimers were introduced into the plasmid pX8δT, successively.

Construction of pX8δT_SBV_L (FIG. 1C): In a multi-step cloning procedure the cDNA clone pX8δT_SBV_L was constituted from five megaprimer PCR fragments which were assembled into plasmid vector pX8δT by fusion PCR. In a first step segment L cDNA was synthesized with primer P_Ph_L1F and P_L3F and used as template for the generation of the megaprimers 1, 2, 3, 4 and 5, respectively. As primers for the generation of megaprimer 1 primers P_Ph_L1F and P_Ph_L1R, for the generation of megaprimer 2 the primers P_L2F and P_Ph_L2R, for the generation of megaprimer 3 the primers P_L3F and P_Ph_L3R, for the generation of megaprimer 4 the primers P_L4F and P_Ph_L4R and for the generation of megaprimer 5 the primers P_L5F and P_Ph_LR were used. By fusion PCR the megaprimers were introduced into the plasmid pX8δT, successively.

Transfection and Recovery of Recombinant SBV

Transfection experiments are done using BHK 21 cells, clone BSR T7/5, stably expressing the phage T7 RNA polymerase (12), according to Lowen et al. (10). About $6\times10^5$ cells grown to 80% confluency are transfected with various amounts of plasmid DNA e.g. 0.25 μg pX8δT_SBV_L, 0.1 μg pX8δT_SBV_S, 1 μg pX8δT_SBV_M using a transfection reagent e.g., Lipofectin (Invitrogen), Lipofectamin (Invitrogen), Superfect (Qiagen) and DAC-30 (Eurogentec) according to suppliers protocols. Transfected cells are incubated for various times (e.g. 4-5 days) at 37° C. The supernatant fluid is collected, clarified by low speed centrifugation and various volumes (e.g 200 μl) are inoculated into highly susceptible cells (KC, BHK 21). Detection of infectious SBV can be done by indirect IF-staining using SBV-specific monoclonal and polyclonal antibodies.

EXAMPLE 2

Establishment of a reverse genetics system using the plasmid pT/riboSM2 for the generation of recombinant SBV, which allows further investigation on the molecular biology of Orthobunyaviruses as well as the generation of save and efficient vaccines.

SBV was isolated from infected cattle and passaged on KC cells and BHK-21 cells. RNA was extracted from infected cells and transcribed into cDNA. PCR fragments of the three RNA segments were amplified by using gene specific primers and were subcloned into the plasmid pX8δT (11) by restrictions-free cloning (13). The resulting plasmids pX8δT_SBV_S, pX8δT_SBV_M and pX8δT_SBV_L contain the full-length antigenome of SBV. Afterwards, by using segment-specific primers and the full-length plasmids as template DNA, full-length PCR fragments were amplified and inserted into plasmid pT/riboSM2 (14) either by restrictions-free cloning or by digestion with appropriate restriction enzymes (e.g. Esp3I, BsmBI) and ligation. The resulting plasmids pT7ribo_SBV_S, pT7ribo_SBV_M and pT7ribo_SBV_L contain the full-length antigenome of SBV.

Transfection experiments are done by using BSR T7/5 cells, stably expressing the phage T7 polymerase (12) and plasmid DNA of all of the three constructs pT7ribo_SBV_S, pT7ribo_SBV_M and pX8δT_SBV_L or pT7ribo_SBV_L. Supernatants of the cells are harvested after various times following transfection and transferred to susceptible cell lines. The cell monolayers are investigated for expression of SBV proteins by indirect immunofluorescence staining.

Results

Three cDNA clones spanning the complete genomic sequence of the segments S, M and L were generated from viral RNA. RNA transcripts were produced by bacteriophage T7 polymerase in BSR T7/5 cells. The exact 3' end of the RNA is specified by self-cleavage of the RNA by the hepatitis delta virus antigenome ribozyme sequence. Rescue of infectious SBV, growth characteristics of recombinant viruses and manipulation of the full-length genome like the deletion of relevant domains can be demonstrated. The virus rescue is more efficient, compared to example 1.

Conclusions

A reverse genetic system for the recovery of SBV, the first European Simbu serogroup virus, can be established. The new system can be used for the generation of recombinant SBV, by transfection of cells stably expressing phage T7 RNA polymerase with the plasmids pT7ribo_SBV_S, pT7ribo_SBV_M and pX8δT_SBV_L or pT7—SBV_L allowing expression of antigenomic SBV RNA and the viral proteins. By using SBV reverse genetics, defined mutants can be designed enabling the mechanistic investigation of virus-host interactions as well as the molecular basis of SBV pathogenesis. Furthermore, the approach will be useful for the design of next generation vaccines like packaged replicons and defective in second cycle virions, chimera or modified deletion mutants.

In the following, the construction of the plasmids pT7ribo_SBV_S, pT7ribo_SBV_M, pX8δT_SBV_L and pT7ribo_SBV_L and the transfection and recovery of recombinant SBV, as mentioned above, is described in closer detail.

Figure 2A:
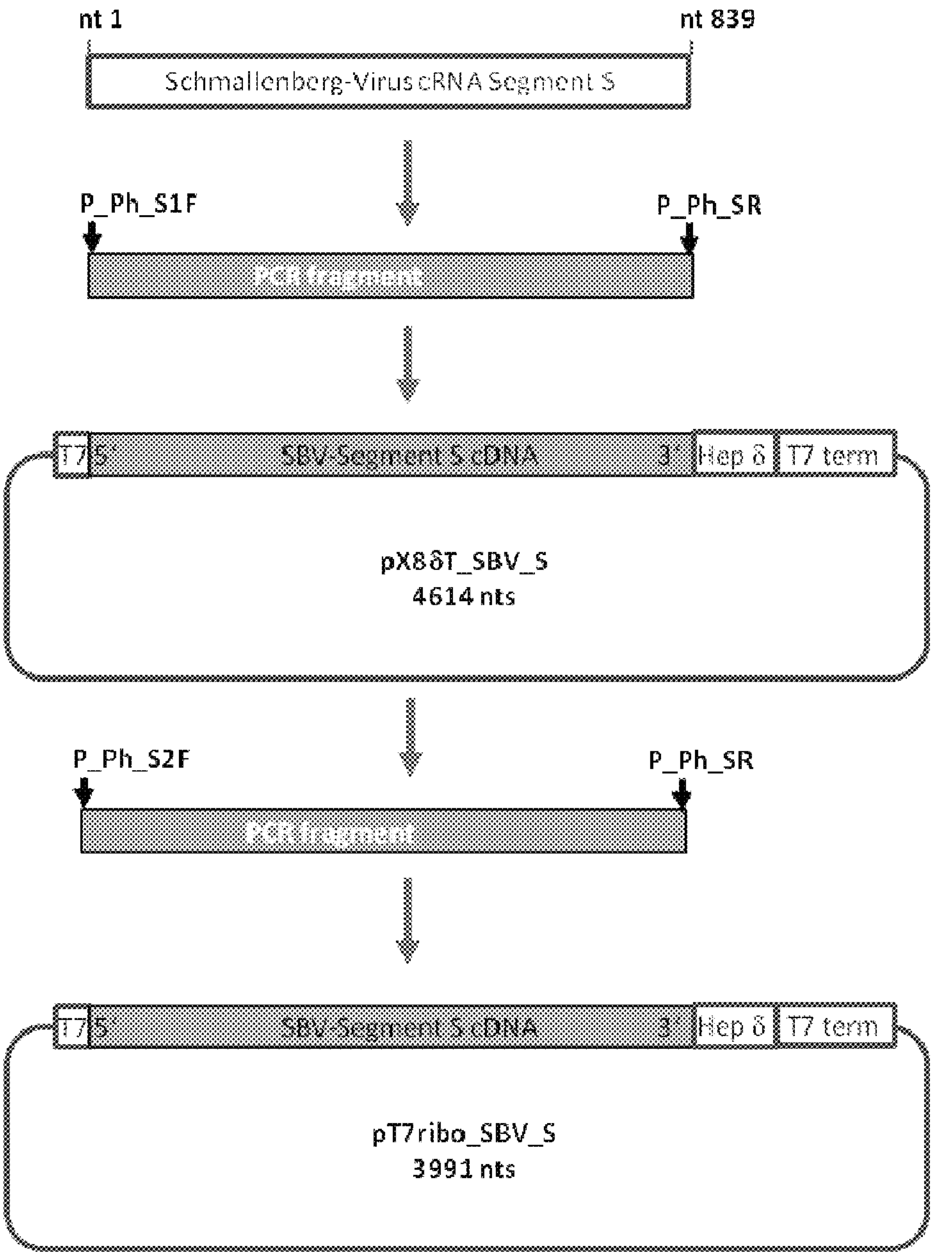
Figure 2B:
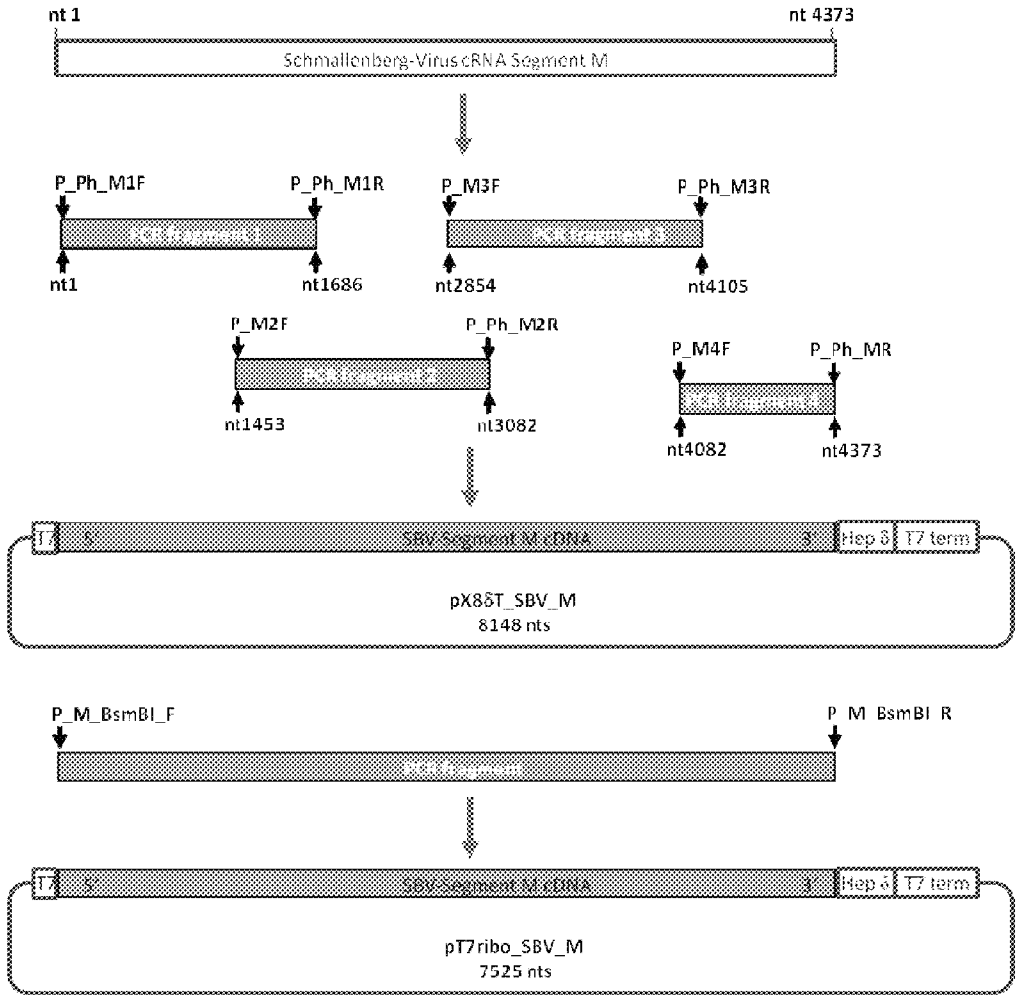
Figure 2C:
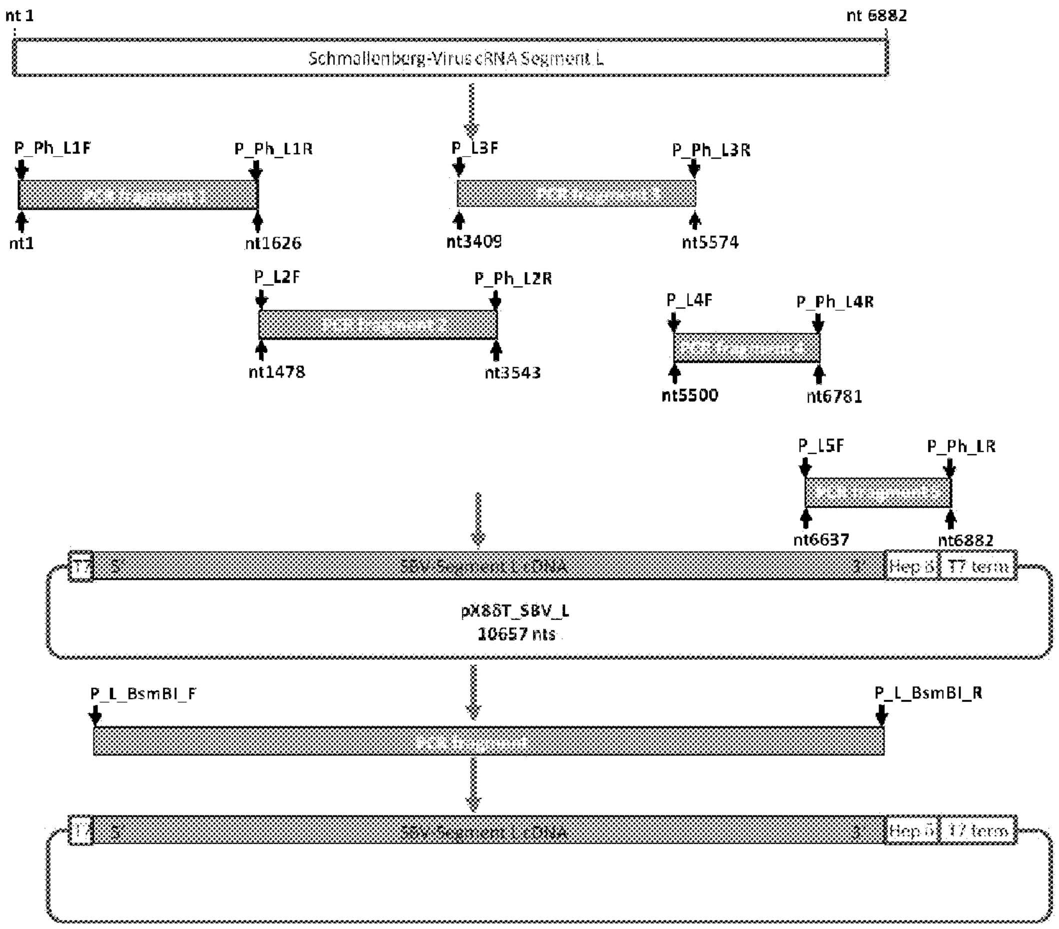

The construction of the plasmids pT7ribo_SBV_S, pT7ribo_SBV_M pX8δT_SBV_L and pT7ribo_SBV_L was done by using the plasmid vectors X8δT (11) and pT7riboSM2 (14). cDNA of the Schmallenberg Virus (SBV) RNA segments was inserted into this plasmid by standard cloning methods using restriction enzyme BsmB or by restriction-free cloning (fusion PCR) (13), respectively. The construction of the cDNA clones is shown in FIG. 2A-2C. The plasmids contain a bacteriophage T7 promotor (T7) before 5' SBV cDNA to enable in vitro transcription of cDNA into RNA, the Hepatitis delta virus ribozyme sequence (Hep δ for the generation of the exact 3' end by self-cleavage of the nascent RNA by the Hepatitis delta virus antigenome ribozyme and the T7 transcription termination sequence (T7 term) downstream the 3' end of the SBV cDNA. Location of the used primers and nucleotide positions corresponding to the Schmallenberg antigenome are indicated by arrows.

RNA of Schmallenberg virus (BH80/11-4) infected BHK 21 cells was isolated by using QIAmp viral RNA Mini Kit (Qiagen) and transcribed by using the Transcriptor High Fidelity cDNA Synthesis Kit (Roche). Plasmids were amplified in *Escherichia coli* DH10B™ cells (Invitrogen). For Megaprimer-PCR and fusion PCR the Phusion High Fidelity PCR Master Mix with HF Buffer (New England Biolabs) and Phusion High-Fidelity Master Mix (Finnzymes) were used. Digestion of the plasmids and DNA fragments was done with The restriction enzymes BsmBI (New England Biolabs) and Esp3I (Fisher Scientific). For ligation of plasmid DNA and DNA fragments, T4 DNA ligase (Promega) was used. Plasmid DNA was purified by using Qiagen Plasmid Mini or Midi Kit (Qiagen). Sequencing was carried out using the Big Dye® Terminator v1.1 Cycle sequencing Kit (Applied Biosystems). Nucleotide sequences were read with an automatic sequencer (3130 Genetic Analyzer, Applied Biosystems) and analyzed using the Genetics Computer Group software version 11.1 (Accelrys Inc., San Diego, USA). Primers were synthesized by biomers.net GmbH and are listed in table 2.

TABLE 2

Nucleotide sequence of PCR primers

| Primer | Sequenz 5' → 3'[a] | Genomic region |
|---|---|---|
| P_Ph_S1F | CTTGTAATACGACTCACTATAGGGAGTAG TGAGCTCCACTATTAAC | 1-22[a] (+sense) |
| P_Ph_S1R | GTGGAGATGCCATGCCGACCCAGTAGTGT TCTCCACTTATTAAC | 830-808[a] (-sense) |
| P_Ph_S2F | CTTGTAATACGACTCACTATAGAGTAGTG AACTCCACTATTAAC | 1-22[a] (+sense) |
| P_Ph_M1F | CTTGTAATACGACTCACTATAGGGAGTAG TGAACTACCACAATC | 1-20[b] (+sense) |
| P_Ph_M1R | GTGGAGATGCCATGCCGACCCGCACTTGG AGAGGGCACAACTG | 1686-1665[b] (-sense) |
| P_M2F | CTCAGCTTACAATAGAGCACC | 1453-1473[b] (+sense) |
| P_Ph_M2R | GTGGAGATGCCATGCCGACCCGTGACCC AACCATCTTGATG | 3080-3063[b] (-sense) |
| P_M3F | TCGAGTCGCACATCCCTGC | 2854-2872[b] (+sense) |
| P_Ph_M3R | GTGGAGATGCCATGCCGACCCGTCAGTCT CCAATaGAAAGATAGG | 4105-4082[b] (-sense) |
| P_M4F | CCTATCTTTCTATTGGAGACTGAC | 4082-4105[b] (+sense) |
| P_Ph_MR | GTGGAGATGCCATGCCGACCCAGTAGTGTTC TACCACATG | 4373-4355[b] (-sense) |
| P_M_BsmBI_F | CTACCGTCTCCTATAGAGTAGTGAACTACCA CAATC | |
| P_M_BsmBI_R | GTACCGTCTCCACCCAGTAGTGTTCTACCACA TG | |
| P_Ph_L1F | CTTGTAATACGACTCACTATAGGGAGTAG TGTACCCCTAATTACAATC | 1-24[c] (+sense) |
| P_Ph_L1R | GTGGAGATGCCATGCCGACCCGTTTGCAC AACACACTACACG | 1626-1606[c] (-sense) |
| P_L2F | GTTCAAAGGATACATGGGATCAG | 1478-1500[c] (+sense) |
| P_Ph_L2R | GTGGAGATGCCATGCCGACCCGTCATCAG AATGAACCATAG | 3543-3524[c] (-sense) |
| P_L3F | CTGCAGGGGAATCTCAATTACAC | 3409-343[c] (+sense) |
| P_Ph_L3R | GTGGAGATGCCATGCCGACCCGATTGATA GATCAATTGGACCAGTAG | 5570-55494[c] (-sense) |
| P_L4F | GCAGAAGAGCAGATCACATGG | 5500-5520[c] (+sense) |
| P_Ph_L4R | AGGTGGAGATGCCATGCCGACCCCAAAC TTTGATCTGCCACCC | 6781-6762[c] (-sense) |
| P_L5F | GAGCCATGGGTGTCTATACTG | 6637-6657[c] (+sense) |
| P_Ph_LR | GTGGAGATGCCATGCCGACCCAGTAGTGT GCCCCTAATTACATG | 6882-6862[c] (-sense) |
| P_Mut L_BsmBIF | GAAAAGTACACCCAGATCTTTGGtGAtGCATT GTCAGAATTGCCGTTTG | 340-388[c] (+sense) |

TABLE 2-continued

Nucleotide sequence of PCR primers

| Primer | Sequenz 5' → 3'[a] | Genomic region |
|---|---|---|
| P_L_BsmBI_F | CTAC*CGTCTC*CTATA*G*AGTAGTGTACCCC TAATTAC | 1-20[c] (+sense) |
| P_L_BsmBI_R | CTAC*CGTCTC*CACCCAGTAGTGTGCCCCT AATTAC | 6882-6859[c] (-sense) |

[a]nucleotide position corresponding to SBV segment S sequence (unpublished)
[b]nucleotide position corresponding to SBV segment M sequence (unpublished)
[c]nucleotide position corresponding to SBV segment L sequence (unpublished)

Sequences derived from plasmids X8δT and pT7riboSM2 are underlined, mutated nucleotides are in lower case and additional G residues and restriction sites are in italics.

Construction of pT7—SBV_S (FIG. 2A): In a first step segment S cDNA was synthesized with primer P_Ph_S1F and used as template for the generation of a megaprimer PCR fragment. As primers P_Ph_S1F and P_Ph_S1R were utilized. By fusion PCR, SBV segment S sequences were introduced into the plasmid pX8δT. Plasmid pX8δT_SBV_S was used as template, to amplify a full-length megaprimer PCR fragment by using primers P_Ph_S2F and P_Ph_S1R. By fusion PCR, SBV segment S sequences were introduced into the plasmid pT7ribo_SM2, resulting in plasmid pT7ribo_SBV_S.

Construction of pT7ribo_SBV_M (FIG. 2B): In a multi-step cloning procedure the cDNA clone pX8δT_SBV_M was constituted from four megaprimer PCR fragments which were assembled into plasmid vector pX8δT by fusion PCR. In a first step segment M cDNA was synthesized with primer P_Ph_M1F and P_M3F and used as template for the generation of the megaprimers 1, 2, 3 and 4, respectively. As primers for the generation of megaprimer 1 primers P_Ph_M1F and P_Ph_M1R, for the generation of megaprimer 2 the primers P_M2F and P_Ph_M2R, for the generation of megaprimer 3 the primers P_M3F and P_Ph_M3R and for the generation of megaprimer 4 the primers P_M4F and P_Ph_MR were used. By fusion PCR the megaprimers were introduced into the plasmid pX8δT, successively. Plasmid pX8δT_SBV_M was used as template, to amplify a full-length PCR fragment by using primers P_M_BsmBI_F and P_M_BsmBI_R. This PCR fragment was digested with BsmBI and ligated into BsmBI-digested plasmid pT7ribo_SM2, resulting in plasmid pT7ribo_SBV_M.

Construction of pX8δT_SBV_L (FIG. 2C): In a multi-step cloning procedure the cDNA clone pX8δT_SBV_L was constituted from five megaprimer PCR fragments which were assembled into plasmid vector pX8δT by fusion PCR. In a first step segment L cDNA was synthesized with primer P_Ph_L1F and P_L3F and used as template for the generation of the megaprimers 1, 2, 3, 4 and 5, respectively. As primers for the generation of megaprimer 1 primers P_Ph_L1F and P_Ph_L1R, for the generation of megaprimer 2 the primers P_L2F and P_Ph_L2R, for the generation of megaprimer 3 the primers P_L3F and P_Ph_L3R, for the generation of megaprimer 4 the primers P_L4F and P_Ph_L4Rand for the generation of megaprimer 5 the primers P_L5F and P_Ph_LR were used. By fusion PCR the megaprimers were introduced into the plasmid pX8δT, successively. In order to generate pT7ribo_SBV_L, the BsmBI-site within pX8δT_SBV_L had to be deleted by site-directed mutagenesis. A PCR fragment (megaprimer) was amplified by using primers P_Mut L_BsmBIF, P_Mut L_BsmBIR and plasmid pX8δT_SBV_L as template DNA. By fusion PCR the megaprimer was introduced into the plasmid pX8δT_SBV_L, resulting in the plasmid pX8δT_Mut_L_BsmBI. Plasmid pX8δT_Mut_L was used as template, to amplify a full-length PCR fragment by using primers P_L_BsmBI_F and P_L_BsmBI_R. This PCR fragment was digested with BsmBI and ligated into BsmBI-digested plasmid pT7ribo_SM2, resulting in plasmid pT7ribo_SBV_L.

Transfection and Recovery of Recombinant SBV

Transfection experiments are done using BHK 21 cells, clone BSR T7/5, stably expressing the phage T7 RNA polymerase (12), according to Lowen et al. (10). About $6\times10^5$ cells grown to 80% confluency are transfected with various amounts of plasmid DNA e.g., 3 μg pT7robo_SBV_S, 3 μg pT7ribo_SBV_M, 3 μg pX8δT_SBV_L or 3 μg pT7ribo_SBV_L using a transfection reagent e.g. Lipofectin (Invitrogen), Lipofectamin (Invitrogen) and Superfect (Qiagen) according to suppliers protocols. Transfected cells are incubated for various times (e.g. 4-5 days) at 37° C. The supernatant fluid is collected, clarified by low speed centrifugation and various volumes (e.g 0.1-1.0 ml) are inoculated into highly susceptible cells (KC, BHK 21). Detection of infectious SBV can be done by indirect IF-staining using SBV-specific monoclonal and polyclonal antibodies.

List Of Figures

FIG. 1A: Construction of the plasmid pX8dT_SBV_S.
FIG. 1B: Construction of the plasmid pX8dT_SBV_M.
FIG. 1C: Construction of the plasmid pX8dT_SBV_L.
FIG. 2A: Construction of the plasmid pT7ribo_SBV_S.
FIG. 2B: Construction of the plasmid pT7ribo_SBV_M.
FIG. 2C: Construction of the plasmid pT7ribo_SBV_L.

In The Sequence Listing

SEQ ID NO:1 corresponds to the complete genome sequence of a S segment of an infectious Schmallenberg virus (BH80/11-4),
SEQ ID NO:2 corresponds to the complete genome sequence of a M segment of an infectious Schmallenberg virus (BH80/11-4),
SEQ ID NO:3 corresponds to the complete genome sequence of a L segment of an infectious Schmallenberg virus (BH80/11-4),
SEQ ID NO:4 corresponds to the sequence of plasmid pX8δT_SBV_S,
SEQ ID NO:5 corresponds to the sequence of plasmid pX8δT_SBV_M,
SEQ ID NO:6 corresponds to the sequence of plasmid pX8δT_SBV_L,
SEQ ID NO: 7 corresponds to SEQ ID NO:1, wherein the nucleotide at position 9 is "a" instead of "g", SEQ ID NO:8 corresponds to the sequence of plasmid pT7ribo_SBV_S, SEQ ID NO:9 corresponds to the sequence of plasmid pT7ribo_SBV_M, SEQ ID NO:10 corresponds to the sequence of plasmid pT7ribo_SBV_L.

References

All references cited herein are entirely incorporated by reference.

1. B. Hoffmann, M. Scheuch, D. Hoper, R. Jungblut, M. Holsteg, H. Schirrmeier, M. Eschbaumer, K. V. Goller, K. Wernike, M. Fischer, A. Breithaupt, T. C. Mettenleiter, M. Beer, Novel orthobunyavirus in Cattle, Europe, 2011. Emerg. Infect. Dis. 18, 469-472 (2012).
2. M.-M. Gariglinany et al., Schmallenberg virus in calf born at term with porencephaly, Belgium. Emerg. Infect. Dis. 18 (2012), doi: 10.3201/eid1806.120104.
3. M. D. Bowen et al., A reassortant bunyavirus isolated from acute hemorrhagic fever cases in Kenya and Somalia. Virology. 291, 185-190 (2001).
4. A. M. Q. King, M. J. Adams, E. B. Carstens, E. J. Lefkowitz, Eds., Virus Taxonomy: Ninth Report of the International Committee on Taxonomy of Viruses. (Elsevier, San Diego, USA, 2011), pp 725-731.
5. R. M. Kinney, C. H. Calisher, Antigenic relationships among Simbu serogroup (Bunyaviridae) viruses. Am. J. Trop. Med. Hyg. 30, 1307-1318 (1981).
6. M. F. Saeed, L. L1, H. Wang, S. C. Weaver, A. D. Barrett, Phylogeny of the Simbu serogroup of the genus Bunyavirus. J. Gen. Virol. 82, 2173-2181 (2001).
7. E. F. Dunn, D. C. Pritlove, H. Jin, R. M. Elliott, Transcription of a recombinant bunyavirus RNA template by transiently expressed bunyavirus proteins. Virology 211 133-143 (1995).
8. X. Shi, A. Kohl, V. H., Leonard, P. Li, A. McLees, R. M. Elliott, Requirement of the N-terminal region of orthobunyavirus nonstructural protein NSm for virus assembly and morphogenesis. J. Virol. 80, 8089-8099 (2006).
9. A. Bridgen, R. M. Elliot, Rescue of a segmented negative-strand RNA virus entirely from cloned complementary DNAs. Proc. Natl. Acad. Sci. U.S.A. 93, 15400-15404 (1996).
10. A. C. Lowen, C. Noonan, A. McLees, R. M. Elliotts, Efficient bunyavirus rescue from cloned cDNA. Virology 330, 493-500 (2004).
11. M. J. Schnell, T. Mebatsion, K. K. Conzelmann, Infectious rabies viruses from cloned cDNA. EMBO Journal 13, 4195-4203 (1994).
12. U. J. Buchholz, S. Finke, K. K. Conzelmann, Generation of bovine respiratory syncytial virus (BRSV) from cDNA: BRSV NS2 is not essential for virus replication in tissue culture, and the human RSV leader region acts as a functional BRSV promotor. J. Virol. 73, 251-259 (1999).
13. M. Geiser, R. Cebe, D. Drewello, R. Schmitz, Integration of PCR fragments at any specific site within cloning vectors without the use of restriction enzymes and DNA ligase. Biotechniques 31, 88-90, 92 (2001).
14. M. Habjan, N. Penski, M. Spiegel, F. Weber, T7 RNA polymerase-dependent and -independent systems for cDNA-based rescue of Rift Valley fever virus. *J Gen Virol* 89, 2157-2166 (2008).

The invention claimed is:

1. A plasmid or cDNA construct encoding a complete antigenomic RNA sequence of a M segment of a Schmallenberg virus (SBV) vRNA genome comprising the cDNA sequence SEQ ID NO:2.

2. A plasmid or cDNA construct encoding a complete antigenomic RNA sequence of an S segment of a Schmallenberg virus (SBV) vRNA genome comprising the cDNA sequence SEQ ID NO:7.

3. A plasmid or cDNA construct encoding a complete antigenomic RNA sequence of a L segment of a Schmallenberg virus (SBV) vRNA genome, comprising inserted material the cDNA sequence SEQ ID NO:3.

4. A combination of two plasmids or cDNA constructs selected from the group consisting of the plasmids or cDNA constructs of claim 1, claim 2, and claim 3.

5. A combination of the plasmids or cDNA constructs of claim 1, claim 2, and claim 3.

6. The combination of claim 5, wherein the plasmids or cDNA constructs contained therein are capable of producing infectious recombinant Schmallenberg virus when transfected into cells.

7. The combination of claim 6, wherein the infectious recombinant virus is able to induce SBV viremia in mammals and/or insects.

8. An isolated cell comprising the plasmid or cDNA construct of claim 1.

9. An isolated cell comprising a combination of plasmids or cDNA constructs according to claim 5.

10. The isolated cell of claim 8, wherein the isolated cell contains an RNA polymerase.

11. The isolated cell of claim 10, wherein the isolated cell expresses the RNA polymerase from a co-transfected expression plasmid.

12. The plasmid or cDNA construct of claim 1, further comprising a combination of at least one second plasmid or cDNA construct comprising a complete antigenomic RNA sequence of a Schmallenberg virus (SBV) vRNA genome segment, wherein said at least one second construct encodes a cDNA sequence selected from the group consisting of:

a) SEQ ID NO:7; b) SEQ ID NO:3; and c) any combinations thereof.

13. The combination of plasmid or cDNA constructs of claim 12, comprising a second plasmid or cDNA construct encoding the nucleic acid sequence of SEQ ID NO:7, and a third plasmid or cDNA construct encoding the nucleic acid sequence of SEQ ID NO:3.

14. The combination of claim 13, wherein the plasmids or cDNA constructs are capable of producing infectious recombinant Schmallenberg virus when said cDNA constructs are transfected into isolated cells.

15. The combination of claim 14, wherein a produced infectious recombinant virus is able to induce SBV viremia in mammals and/or insects.

16. An isolated cell comprising a combination of plasmids or cDNA constructs according to claim 13.

* * * * *